(12) United States Patent
Calarese et al.

(10) Patent No.: US 11,098,107 B2
(45) Date of Patent: Aug. 24, 2021

(54) ANTIBODIES WITH ENGINEERED CH2 DOMAINS, COMPOSITIONS THEREOF AND METHODS OF USING THE SAME

(71) Applicant: SUTRO BIOPHARMA, INC., South San Francisco, CA (US)

(72) Inventors: Daniel Calarese, Redwood City, CA (US); Gang Yin, South San Francisco, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 281 days.

(21) Appl. No.: 16/309,821

(22) PCT Filed: Jun. 14, 2017

(86) PCT No.: PCT/US2017/037545
§ 371 (c)(1),
(2) Date: Dec. 13, 2018

(87) PCT Pub. No.: WO2017/218698
PCT Pub. Date: Dec. 21, 2017

(65) Prior Publication Data
US 2019/0177404 A1    Jun. 13, 2019

Related U.S. Application Data

(60) Provisional application No. 62/350,640, filed on Jun. 15, 2016.

(51) Int. Cl.
| | | |
|---|---|---|
| *C07K 16/18* | (2006.01) | |
| *C07K 16/00* | (2006.01) | |
| *A61P 37/06* | (2006.01) | |
| *A61P 35/00* | (2006.01) | |
| *C12N 15/85* | (2006.01) | |
| *A61K 47/68* | (2017.01) | |

(52) U.S. Cl.
CPC .............. *C07K 16/18* (2013.01); *A61P 35/00* (2018.01); *A61P 37/06* (2018.01); *C07K 16/00* (2013.01); *C12N 15/85* (2013.01); *A61K 47/6803* (2017.08); *C07K 2317/41* (2013.01); *C07K 2317/522* (2013.01); *C07K 2317/524* (2013.01); *C07K 2317/90* (2013.01); *C07K 2317/94* (2013.01); *C12N 2015/8518* (2013.01)

(58) Field of Classification Search
CPC .......... C07K 2317/41; C07K 2317/522; C07K 16/00; A61K 47/6803
See application file for complete search history.

(56) References Cited

U.S. PATENT DOCUMENTS

| | | | |
|---|---|---|---|
| 2005/0054832 A1 | 3/2005 | Lazar et al. | |
| 2007/0111281 A1* | 5/2007 | Sondermann | A61P 35/00 435/69.1 |
| 2015/0017187 A1* | 1/2015 | Thanos | C12N 15/09 424/178.1 |

FOREIGN PATENT DOCUMENTS

| | | |
|---|---|---|
| WO | WO 2006/019447 A1 | 2/2006 |
| WO | WO 2011/091078 A2 | 7/2011 |

OTHER PUBLICATIONS

International Search Report and Written Opinion of the International Searching Authority of PCT/US2017/037545 dated Nov. 14, 2017, 14 pages.
Ishino et al., "Engineering a Monomeric Fc Domain Modality by N-Glycosylation for the Half-life Extension of Biotherapeutics", Journal of Biological Chemistry, American Society For Biochemistry And Molecular Biology, US, vol. 288, No. 23, Jun. 7, 2013, pp. 16529-16537.

* cited by examiner

*Primary Examiner* — Peter J Reddig
*Assistant Examiner* — Cheng Lu
(74) *Attorney, Agent, or Firm* — Squire Patton Boggs (US) LLP

(57) ABSTRACT

The present disclosure relates to antibodies and antibody conjugates having one or more site-specific mutations in the CH2 domain of the heavy chain. The antibody variants disclosed herein can have improved characteristics (e.g., thermal stability, antibody yields, antibody titers, cell-killing) relative to a parent or wild type antibody, including aglycosylated parent or wild type antibodies. Pharmaceutical compositions, diagnostic compositions and kits comprising the same, as well as methods of using these compositions and kits for therapeutic and diagnostic purposes, are also described.

25 Claims, 15 Drawing Sheets
Specification includes a Sequence Listing.

SEQUENCE LISTING

```
<160> NUMBER OF SEQ ID NOS: 1

<210> SEQ ID NO 1
<211> LENGTH: 252
<212> TYPE: PRT
<213> ORGANISM: Artificial Sequence
<220> FEATURE:
<223> OTHER INFORMATION: Synthetic: IgG1 Fc domain

<400> SEQUENCE: 1

Ala Ala Gly Ser Asp Gln Glu Pro Lys Ser Ser Asp Lys Thr His Thr
1               5                   10                  15

Cys Pro Pro Cys Ser Ala Pro Glu Leu Leu Gly Gly Ser Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175
```

```
Gln Pro Glu Asn Asn Tyr Lys Thr Thr Pro Pro Val Leu Asp Ser Asp
            180             185             190
Gly Ser Phe Phe Leu Tyr Ser Lys Leu Thr Val Asp Lys Ser Arg Trp
        195             200             205
Gln Gln Gly Asn Val Phe Ser Cys Ser Val Met His Glu Ala Leu His
    210             215             220
Asn His Tyr Thr Gln Lys Ser Leu Ser Leu Ser Pro Gly Lys Gly Ser
225             230             235             240
Gly Asp Tyr Lys Asp Asp Asp Lys Gly Ser Gly
            245             250
```

ANTIBODIES WITH ENGINEERED CH2 DOMAINS, COMPOSITIONS THEREOF AND METHODS OF USING THE SAME

CROSS-REFERENCE TO RELATED APPLICATION

This application is a filing under 35 U.S.C. § 371 of International Patent Application No. PCT/US2017/037545, filed Jun. 14, 2017, which claims the benefit of U.S. Provisional Patent Application No. 62/350,640, filed Jun. 15, 2016. Each of the foregoing applications is incorporated herein by reference in its entirety.

REFERENCE TO SEQUENCE LISTING SUBMITTED VIA EFS-WEB

This application includes an electronically submitted sequence listing in .txt format. The .txt file contains a sequence listing entitled "108843 00196 ST25.txt," created Dec. 12, 2018, and is 3 kilobytes in size. The sequence listing contained in this .txt file is part of the specification and is incorporated herein by reference in its entirety.

FIELD OF THE INVENTION

The present disclosure generally relates to antibodies with engineered CH2 domains, which illustrate improved effects (e.g. thermal stability, improved antibody yields, improved antibody titers). Also provided are pharmaceutical compositions, diagnostic compositions and kits containing the antibodies disclosed herein as well as methods of using the same for therapeutic and diagnostic purposes.

BACKGROUND

In mammalian antibodies, glycosylation of the Fc region can play an important role in antibody effector functions. For example, in immunoglobulin G (IgG), glycosylation can affect Fc-mediated effector functions such as complement activation and engagement of receptors for the Fc region of IgG. However, variations in the conditions of production systems can influence the glycosylation of antibodies. Such variations can affect the biological activities of antibody products and lead to potency changes in antibodies and antibody conjugates. Accordingly, the use of glycoengineering may be employed to provide antibodies with specific glycoforms in order to achieve a desired therapeutic effect.

Aglycosylated (or deglycosylated) antibodies are often selected when an effector function is not desired or is not important. In some circumstances, a host cell or cell-free system selected for antibody production (e.g. a prokaryotic cell system or a non-glycosylating mammalian cell system) lacks native tools for glycosylating a desired antibody. Aglycosylated antibodies can suffer from lower thermal stability or higher aggregation rates relative to the glycosylated version of the same antibodies (Zheng et al, 2011, *mAbs* 3(6):568-576). Accordingly, there is a need for aglycosylated (or deglycosylated) antibodies with properties that are similar and/or more aligned with glycosylated versions of the same antibodies.

SUMMARY

Embodiments are directed to an antibody including at least one amino acid substitution in the CH2 domain of the heavy chain, wherein the at least one amino acid substitution is selected from the group consisting of: V262E, V262D, V262K, V262R, V262S, V264S, V303R, and V305R, and combinations thereof. In some embodiments, the at least one amino acid substitution is selected from the group consisting of: V262E, V262D, V262K, V262R, and V262S. In some embodiments, the at least one amino acid substitution is selected from the group consisting of: V262E, V262K, and V262S. In some embodiments, the at least one amino acid substitution is V262E. In some embodiments, the at least one amino acid substitution is V264S. In some embodiments, the at least one amino acid substitution is V303R. In some embodiments, the at least one amino acid substitution is V305R.

In some embodiments, the antibody further includes an amino acid substitution at position F241 and/or F243 of the CH2 domain. In some embodiments, the amino acid substitution is at F241 of the CH2 domain. In some embodiments, the amino acid substitution is at F243 of the CH2 domain.

In certain embodiments wherein the antibody contains at least one amino acid substitution selected from V264S, V303R, and V305R, the antibody further includes an amino acid substitution that is V262T. In some embodiments, the antibody further includes an amino acid substitution at position F241 and/or F243 of the CH2 domain. In some embodiments, the amino acid substitution is at F241 of the CH2 domain. In some embodiments, the amino acid substitution is at F243 of the CH2 domain. In some embodiments, the antibody further includes an amino acid substitution at F241 and F243 of the CH2 domain.

In some embodiments, the antibody includes at least two amino acid substitutions in the CH2 domain. In some embodiments, the antibody includes at least three amino acid substitutions in the CH2 domain.

In some embodiments, including any of the foregoing embodiments, the antibody is an aglycosylated or deglycosylated antibody.

In any of the foregoing embodiments, the antibody can further include at least one non-natural amino acid residue. In some embodiments, the at least one non-natural amino acid is at a site in the antibody heavy chain polypeptide. In some embodiments, the at least one non-natural amino acid is at a site in the antibody light chain polypeptide.

In certain embodiments, the antibody includes at least a second non-natural amino acid. In some embodiments, the at least second non-natural amino acid is inserted at a site in the antibody heavy chain polypeptide. In some embodiments, the at least second non-natural amino acid is inserted at a site in the antibody light chain polypeptide.

In any of the foregoing embodiments, the antibody can include a heavy chain of a type selected from the group consisting of α, δ, ε, and μ.

In any of the foregoing embodiments, the antibody can include a light chain of a type selected from λ and κ.

In any of the foregoing embodiments, the antibody can be of a class or subclass selected from the group consisting of IgA, IgA1, IgA2, IgD, IgE, IgG, IgG1, IgG2, IgG3 and IgM.

In any of the foregoing embodiments, the antibody can be in a form selected from the group consisting of Fv, Fc, Fab, (Fab')$_2$, single chain Fv (scFv), and full-length antibody.

In certain embodiments wherein the antibody further includes at least one non-natural amino acid residue, that at least one non-natural amino acid residue can contain a moiety selected from the group consisting of amino, carboxy, acetyl, hydrazino, hydrazido, semicarbazido, sulfanyl, azido, alkynyl, and tetrazine. In some embodiments, the at least one non-natural amino acid residue includes an azide moiety. In some embodiments, that at least non-natural amino acid residue includes a tetrazine moiety. In some embodiments, the at least one non-natural amino acid residue is para-azido phenylalanine or para-azido methyl phenylalanine.

In certain embodiments wherein the antibody further includes at least a second non-natural amino acid residue, the at least second non-natural amino acid residue can contain a moiety selected from the group consisting of amino, carboxy, acetyl, hydrazino, hydrazido, semicarbazido, sulfanyl, azido, alkynyl, and tetrazine. In some embodiments, the at least second non-natural amino acid residue comprises an azide moiety. In some embodiments, the at least second non-natural amino acid residue comprises a tetrazine moiety. In some embodiments, the at least second non-natural amino acid residue is para-azido phenylalanine or para-azido methyl phenylalanine. In some embodiments, the at least one non-natural amino acid includes an azide moiety and the at least second non-natural amino acid includes a tetrazine moiety. In some embodiments, the at least one non-natural amino acid residue includes a tetrazine moiety and the at least second non-natural amino acid residue includes an azide moiety.

Embodiments are also directed to an antibody conjugate containing the antibody of any of the foregoing embodiments linked to one or more therapeutic moieties or labeling moieties. In some embodiments, the antibody is linked to one or more drugs or polymers. In some embodiments, the antibody is linked to one or more labeling moieties. In some embodiments, the antibody is linked to one or more single-chain binding domains (scFv).

In some embodiments, the antibody conjugate includes at least one of the therapeutic therapeutic moieties or labeling moieties linked to the antibody via a residue of a non-natural amino acid containing an azide moiety. In some embodiments, the antibody conjugate includes at least one of the therapeutic moieties or labeling moieties linked to the antibody via a residue of a non-natural amino acid containing a tetrazine moiety.

In some embodiments, the antibody conjugate includes at least one of the therapeutic moieties or labeling moieties linked to the antibody via a residue of a non-natural amino acid containing an azide moiety and at least one of the therapeutic moieties or labeling moieties linked to the antibody via a residue of a non-natural amino acid containing a tetrazine moiety. In some embodiments, a first therapeutic moiety is linked to the antibody via a residue of the non-natural amino acid containing an azide moiety, and a second therapeutic moiety is linked to the antibody via a residue of the non-natural amino acid containing a tetrazine moiety. In some embodiments, a first labeling moiety is linked to the antibody via a residue of the non-natural amino acid containing an azide moiety, and a second labeling moiety is linked to the antibody via a residue of the non-natural amino acid containing a tetrazine moiety. In some embodiments, a therapeutic moiety is linked to the antibody via a residue of the non-natural amino acid containing an azide moiety, and a labeling moiety is linked to the antibody via a residue of the non-natural amino acid containing a tetrazine moiety. In some embodiments, a labeling moiety is linked to the antibody via a residue of the non-natural amino acid containing an azide moiety, and a therapeutic moiety is linked to the antibody via a residue of the non-natural amino acid containing a tetrazine moiety.

In some embodiments, the antibody conjugate includes the antibody linked to the one or more therapeutic moieties or labeling moieties via one or more linkers.

In some embodiments, the antibody conjugate has a melting temperature within about five degrees Celsius of a parent antibody. In some embodiments, the antibody conjugate has a melting temperature within about four degrees Celsius of the parent antibody. In some embodiments, the antibody conjugate has a melting temperature within about three degrees Celsius of the parent antibody. In some embodiments, the antibody conjugate has a melting temperature within about two degrees Celsius of the parent antibody. In some embodiments, the melting temperature is selected from the group consisting of TM1 and TM2.

Disclosed herein is a composition including the antibody or antibody conjugate of any of the foregoing embodiments, wherein the antibody or antibody conjugate is substantially pure.

Also disclosed herein is a composition including the antibody or antibody conjugate of any of the foregoing embodiments, wherein the antibody or antibody conjugate is at least 95% by mass of the total antibody or antibody conjugate mass of the composition.

Embodiments are directed to a pharmaceutical composition containing the antibody or antibody conjugate of any of the foregoing embodiments and a pharmaceutically acceptable carrier.

Also provided herein is a kit containing the antibody or antibody conjugate of any of the foregoing embodiments, and instructions for use of the antibody. In some embodiments, the antibody or antibody conjugate is lyophilized. In some embodiments, the kit further includes a fluid for reconstitution of the lyophilized antibody or lyophilized antibody conjugate.

Embodiments are directed to a polynucleotide encoding an antibody of any of the foregoing embodiments and a vector containing the same. Also provided herein is a host cell containing the vector encoding the antibody. In some embodiments, the host cell is selected from a bacterial cell, a fungal cell, and a mammalian cell. In some embodiments, the host cell is selected from an *E. coli* cell, a *Saccharomyces cerevisiae* cell, and a CHO cell.

Embodiments are also directed to a method of treating, preventing or diagnosing a disease or condition in a subject in need thereof, wherein the method includes administering to the subject an effective amount of the antibody or antibody conjugate of any of the foregoing embodiments, or a composition or a pharmaceutical composition containing the same. In some embodiments, the disease or condition is selected from a cancer, an autoimmune disease, an inflammatory disease, and an infection. In some embodiments, the effective amount is a therapeutically effective amount.

Embodiments disclosed herein are also directed to the use of the antibody or antibody conjugate of any of the foregoing embodiments for treating, preventing or diagnosing a disease or condition in a subject in need thereof. In some embodiments, the disease or condition is selected from a cancer, an autoimmune disease, an inflammatory disease, and an infection.

These and other embodiments along with many of its features are described in more detail in conjunction with the text below and attached figures.

DETAILED DESCRIPTION OF THE EMBODIMENTS

Figure 1:
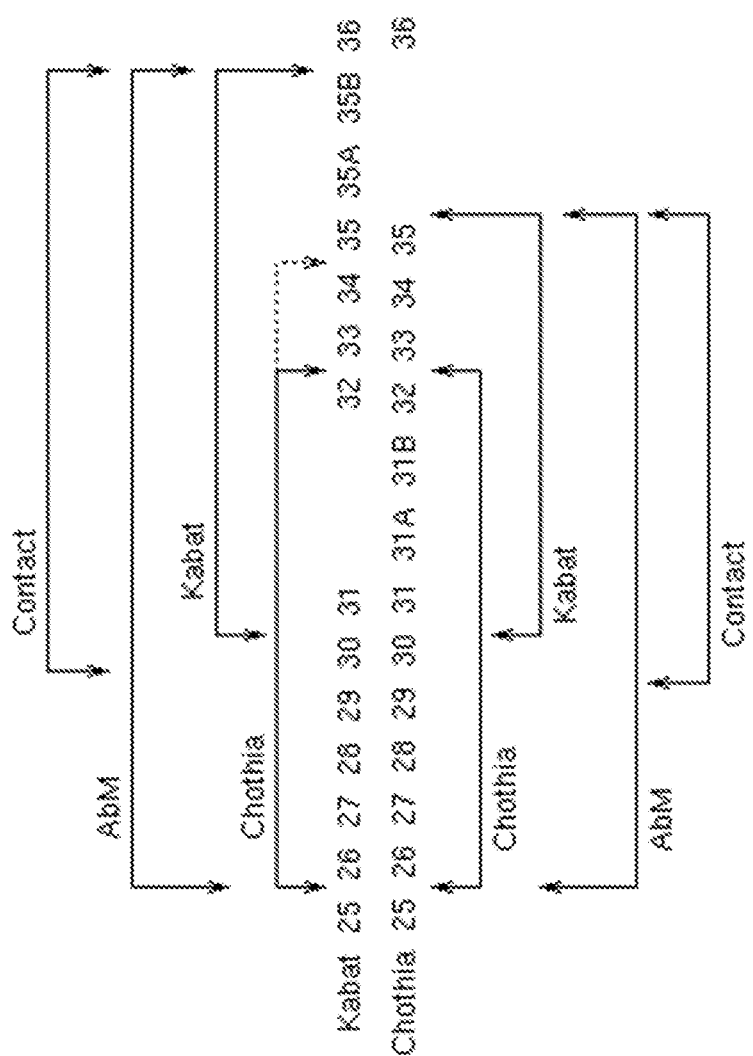
FIG. 1 provides a comparison of the Kabat and Chothia numbering systems for CDR-H1. See Martin A. C. R. (2010). Protein Sequence and Structure Analysis of Antibody Variable Domains. In R. Kontermann & S. Dübel (Eds.), *Antibody Engineering* vol. 2 (pp. 33-51). Springer-Verlag, Berlin Heidelberg.

Provided herein are antibodies and antibody conjugates and compositions comprising the same, wherein the antibodies comprise at least one amino acid substitution at a specific site in the CH2 domain of the heavy chain. As disclosed herein, the insertion of at least one amino acid substitution at a specific site within the CH2 domain can improve the characteristics of an antibody variant relative to a wild type (i.e., parent) antibody. For example, amino acid substitutions within the CH2 domain as disclosed herein can lead to improved or comparable yields, assembly efficiencies, and/or thermal stability in antibody variants relative to a wild type antibody. This can lead to advantages with respect to the manufacture of antibody products, particularly with respect to bioprocess development.

In some embodiments, the antibodies and/or antibody conjugates provided herein are advantageous in aglycosylated or deglycosylated forms. Such embodiments can provide a means of bypassing or limiting issues associated with glycan heterogeneity in conventionally manufactured glycosylated antibodies.

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* $4^{th}$ ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value.

The term "combinations thereof" includes every possible combination of elements to which the term refers to. For example, a sentence stating that "if $\alpha_2$ is A, then $\alpha_3$ is not D; $\alpha_5$ is not S; or $\alpha_6$ is not S; or combinations thereof" includes the following combinations when $\alpha_2$ is A: (1) $\alpha_3$ is not D; (2) $\alpha_5$ is not S; (3) $\alpha_6$ is not S; (4) $\alpha_3$ is not D; $\alpha_5$ is not S; and $\alpha_6$ is not S; (5) $\alpha_3$ is not D and $\alpha_5$ is not S; (6) $\alpha_3$ is not D and $\alpha_6$ is not S; and (7) $\alpha_5$ is not S and $\alpha_6$ is not S.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$ or VH) and a heavy chain constant region ($C_H$ or CH). The heavy chain constant region typically comprises three domains, abbreviated $C_H1$ (or CH1), $C_H2$ (or CH2), and $C_H3$ (or CH3). Each light chain typically comprises a light chain variable region ($V_L$ or VL) and a light chain constant region. The light chain constant region typically comprises one domain, abbreviated $C_L$ or CL.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at www.bio-inf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_H1$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). "Antibodies from *Escherichia coli*." In Rosenberg M. & Moore G. P. (Eds.), *The Pharmacology of Monoclonal Antibodies*, Vol. 113 (pp. 269-315), Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ zor $V_L$-$V_H$). Any suitable Fc domain known in the art or described herein may be used. In some cases, the Fc domain comprises an IgG1 Fc domain (e.g., SEQ ID NO: 1).

(SEQ ID NO: 1)
AAGSDQEPKSSDKTHTCPPCSAPELLGGSSVFLFPPKPKDTLMISRTPE

VTCVVVDVSHEDPEVKFNWYVDGVEVHNAKTKPREEQYNSTYRVVSVLT

-continued

VLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFF

LYSKLTVDKSRWQQGNVFSCSVMHEALHNHYTQKSLSLSPGKGSGDYKD

DDDKGSG

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

The term "substantially pure" with respect to a composition comprising an antibody refers to a composition that includes at least 80%, 85%, 90% or 95% by weight or, in certain embodiments, 95%, 98%, 99% or 100% by weight, e.g. dry weight, of the antibody relative to the remaining portion of the composition. The weight percentage can be relative to the total weight of protein in the composition or relative to the total weight of antibodies in the composition. Purity can be determined by techniques apparent to those of skill in the art, for instance SDS-PAGE.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" or "$K_a$" ($M^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology,* 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.,* 1994, 91:3809-3813); Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

When used herein in the context of two or more antibodies, the term "competes with" or "cross-competes with" indicates that the two or more antibodies compete for binding to an antigen. In one exemplary assay, an antigen is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. Polypeptide sequences having such substitutions are known as "conservatively modified variants." By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder.

As used herein, the term "subject" means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has a cancer, an inflammatory disease or condition, or an autoimmune disease or condition, that can be treated or diagnosed with an antibody provided herein. In some embodiments, the subject is a human that has or is suspected to have cancer, an inflammatory disease or condition, or an autoimmune disease or condition.

Antibodies

The CH2 domain in antibody heavy chains is typically glycosylated. The CH2 domain has an exposed hydrophobic patch to accommodate the sugar attached during glycosylation of the domain. In certain embodiments disclosed herein, the exposed hydrophobic patch of the CH2 domain was investigated to develop amino acid substitutions that result in improved stability of the antibody and/or corresponding Fc fragment.

Provided herein is an antibody that comprises at least one amino acid substitution in the CH2 domain of an antibody heavy chain. In some embodiments, the antibody comprises at least two amino acid substitutions in the CH2 domain. In some embodiments, the antibody comprises at least three, four, five or six amino acid substitutions in the CH2 domain. In some embodiments, the amino acid substitution is a conservative amino acid substitution as described herein.

The at least one amino acid substitution can be made by standard techniques. In certain embodiments, the substitution is made by one or more mutations in the genetic sequence encoding the CH2 domain of an antibody heavy chain.

Similarly, the at least two amino acid substitutions in the CH2 domain can be made by standard techniques. In certain embodiments, the at least two amino acid substitutions are made by two or more mutations in the genetic sequence encoding the CH2 domain. In some embodiments, the at least three, four, five, or six amino acid substitutions in the CH2 domain can be made by standard techniques. In certain embodiments, the at least three, four, five, or six amino acid substitutions are made by three or more mutations in the genetic sequence encoding the CH2 domain.

In some embodiments, the antibody contains an amino acid substitution in at least one amino acid position selected from the group consisting of: F241, F243, V262, V264, V303 and V305 of the CH2 domain. In some embodiments, the antibody contains an amino acid substitution at an amino acid position selected from the group consisting of: F241, F243, V262, V264, V303 and V305 of the CH2 domain. For example, the antibody can have a single amino acid substitution at F241, F243, V262, V264, V303 or V305 of the CH2 domain. In some embodiments, the antibody contains a single amino acid substitution at F241 of the CH2 domain. In some embodiments, the antibody contains a single amino acid substitution at F243 of the CH2 domain. In some embodiments, the antibody contains a single amino acid substitution at V262 of the CH2 domain. In some embodiments, the antibody contains a single amino acid substitution at V264 of the CH2 domain. In some embodiments, the antibody contains a single amino acid substitution at V303 of the CH2 domain. In some embodiments, the antibody contains a single amino acid substitution at V305 of the CH2 domain.

In some embodiments, the antibody contains an amino acid substitution in at least two amino acid positions selected from the group consisting of: F241, F243, V262, V264, V303, and V305 of the CH2 domain. For example, the antibody can have an amino acid substitution in any two amino acid positions selected from the group consisting of: F241, F243, V262, V264, V303, and V305 of the CH2 domain. In some embodiments, the antibody has an amino acid substitution at F241 and F243 of the CH2 domain. In some embodiments, the antibody has an amino acid substitution at F241 and V262 of the CH2 domain. In some embodiments, the antibody has an amino acid substitution at F241 and V264 of the CH2 domain. In some embodiments, the antibody has an amino acid substitution at F241 and V303 of the CH2 domain. In some embodiments, the antibody has an amino acid substitution at F241 and V305 of the CH2 domain. In some embodiments, the antibody has an amino acid substitution at F243 and V262 of the CH2 domain. In some embodiments, the antibody has an amino acid substitution at F243 and V264 of the CH2 domain. In some embodiments, the antibody has an amino acid substitution at F243 and V303 of the CH2 domain. In some embodiments, the antibody has an amino acid substitution at F243 and V305 of the CH2 domain. In some embodiments, the antibody has an amino acid substitution at V262 and V264 of the CH2 domain. In some embodiments, the antibody has an amino acid substitution at V262 and V303 of the CH2 domain. In some embodiments, the antibody has an amino acid substitution at V262 and V305 of the CH2 domain. In some embodiments, the antibody has an amino acid substitution at V264 and V303 of the CH2 domain. In some embodiments, the antibody has an amino acid substitution at V264 and V305 of the CH2 domain. In some embodiments, the antibody has an amino acid substitution at V303 and V305 of the CH2 domain.

In some embodiments, the antibody contains an amino acid substitution in at least three amino acid positions selected from the group consisting of: F241, F243, V262, V264, V303, and V305 of the CH2 domain. For example, the antibody can contain an amino acid substitution in any three amino acid positions selected from the group consisting of: F241, F243, V262, V264, V303, and V305 of the CH2 domain. In some embodiments, the antibody has an amino acid substitution at F241, F243, and V262 of the CH2 domain. In some embodiments, the antibody has an amino acid substitution at F241, F243, and V264 of the CH2 domain. In some embodiments, the antibody has an amino acid substitution at F241, F243, and V303 of the CH2 domain. In some embodiments, the antibody has an amino acid substitution at F241, F243, and V305 of the CH2 domain. In some embodiments, the antibody has an amino acid substitution at F243, V262, and V264 of the CH2 domain. In some embodiments, the antibody has an amino acid substitution at F243, V262, and V303 of the CH2 domain. In some embodiments, the antibody has an amino acid substitution at F243, V262, and V305 of the CH2 domain. In some embodiments, the antibody has an amino acid substitution at V262, V264, and V303 of the CH2 domain. In some embodiments, the antibody has an amino acid substitution at V262, V264, and V305 of the CH2 domain. In some embodiments, the antibody has an amino acid substitution at V264, V303, and V305 of the CH2 domain.

In some embodiments, the antibody contains an amino acid substitution in at least four amino acid positions selected from the group consisting of: F241, F243, V262, V264, V303, and V305 of the CH2 domain. For example, the antibody can have an amino acid substitution at any four amino acid positions selected from the group consisting of: F241, F243, V262, V264, V303, and V305 of the CH2 domain. In some embodiments, the antibody can have an amino acid substitution at F241, F243, V262, and V264 of the CH2 domain. In some embodiments, the antibody can have an amino acid substitution at F241, F243, V262, and V303 of the CH2 domain. In some embodiments, the antibody can have an amino acid substitution at F241, F243, V262, and V305 of the CH2 domain. In some embodiments, the antibody can have an amino acid substitution at F243, V262, V264, and V303 of the CH2 domain. In some embodiments, the antibody can have an amino acid substitution at F243, V262, V264, and V305 of the CH2 domain. In some embodiments, the antibody can have an amino acid substitution at V262, V264, V303, and V305 of the CH2 domain.

In some embodiments, the antibody contains an amino acid substitution in at least five amino acid positions selected from the group consisting of: F241, F243, V262, V264, V303, and V305 of the CH2 domain. For example, the antibody can have an amino acid substitution at any five amino acid positions selected from the group consisting of: F241, F243, V262, V264, V303, and V305 of the CH2 domain. In some embodiments, the antibody can have an amino acid substitution at F241, F243, V262, V264, and V303 of the CH2 domain. In some embodiments, the antibody can have an amino acid substitution at F241, F243, V262, V264, and V305 of the CH2 domain. In some embodiments, the antibody can have an amino acid substitution at F243, V262, V264, V303, and V305 of the CH2 domain.

In some embodiments, the antibody contains an amino acid substitution at each of: F241, F243, V262, V264, V303, and V305 of the CH2 domain.

In some embodiments, the antibody contains an amino acid substitution at F241 of the CH2 domain. In some embodiments, the amino acid substitution is F241D, F241E, F241K, F241R, F241H, F241S, F241T, F241N, or F241 Q. In some embodiments, the amino acid substitution is F241S, F241R, or F241Y. In some embodiments, the amino acid substitution is F241S. In some embodiments, the amino acid substitution is F241R. In some embodiments, the amino acid substitution is F241Y.

In some embodiments, the antibody contains an amino acid substitution at F243 of the CH2 domain. In some embodiments, the amino acid substitution is F243D, F243E, F243K, F243R, F243H, F243S, F243T, F243N, or F243Q. In some embodiments, the amino acid substitution is F243S or F243R. In some embodiments, the amino acid substitution is F243S. In some embodiments, the amino acid substitution is F243R.

In some embodiments, the antibody contains an amino acid substitution at V262 of the CH2 domain. In some embodiments, the amino acid substitution is V262D, V262E, V262K, V262R, V262H, V262S, V262N, or V262Q. In some embodiments, the amino acid substitution is V262D, V262E, V262K, V262R, or V262S. In some embodiments, the amino acid substitution is V262E, V262K, or V262S. In some embodiments, the amino acid substitution is V262D. In some embodiments, the amino acid substitution is V262E. In some embodiments, the amino acid substitution is V262K. In some embodiments, the amino acid substitution is V262R. In some embodiments, the amino acid substitution is V262S.

In some embodiments, the antibody contains an amino acid substitution at V264 of the CH2 domain. In some embodiments, the amino acid substitution is V264D, V264E, V264K, V264R, V264H, V264S, V264T, V264N, or V264Q. In some embodiments, the amino acid substitution is V264S or V264R. In some embodiments, the amino acid substitution is V264S. In some embodiments, the amino acid substitution is V264R.

In some embodiments, the antibody contains an amino acid substitution at V303 of the CH2 domain. In some embodiments, the amino acid substitution is V303D, V303E, V303K, V303R, V303H, V303S, V303T, V303N, or V303Q. In some embodiments, the amino acid substitution is V303T or V303R. In some embodiments, the amino acid substitution is V303T. In some embodiments, the amino acid substitution is V303R.

In some embodiments, the antibody contains an amino acid substitution at V305 of the CH2 domain. In some embodiments, the amino acid substitution is V305D, V305E, V305K, V305R, V305H, V305S, V305T, V305N, or V305Q. In some embodiments, the amino acid substitution is V305T or V305R. In some embodiments, the amino acid substitution is V305T. In some embodiments, the amino acid substitution is V305R.

In some embodiments, the antibody contains two or more amino acid substitutions in the CH2 domain. In some embodiments, the antibody contains the amino acid mutations V262E and V264S. In some embodiments, the antibody contains the amino acid mutations V262E and V303R. In some embodiments, the antibody contains the amino acid mutations V262E and V305R. In some embodiments, the antibody contains the amino acid mutations V264S and V303R. In some embodiments, the antibody contains the amino acid mutations V264S and V305R. In some embodiments, the antibody contains the amino acid mutations V303R and V305R. In some embodiments, the antibody contains the amino acid mutations V262E, V264S, and V303R. In some embodiments, the antibody contains the amino acid mutations V262E, V264S, and V305R. In some embodiments, the antibody contains the amino acid mutations V262E, V303R, and V305R. In some embodiments, the antibody contains the amino acid mutations V264S, V303R, and V305R. In some embodiments, the antibody contains the amino acid mutations V262E, V264S, V303R, and V305R. In certain embodiments, provided herein are any of the above antibodies additionally containing the amino acid mutation V262T.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e. antigens.

In some embodiments, the amino acid-substituted CH2 domain is part of a heavy chain selected from IgA, IgD, IgE, IgG, and IgM. In some aspects, the heavy chain is selected from IgG1, IgG2, IgG3, IgG4, IgA1, and IgA2.

In some embodiments, the antibody comprises a light chain. In some aspects, the light chain is selected from a kappa (κ) light chain and a lambda (λ) light chain.

In some embodiments, the antibody is an antibody fragment. In some aspects, the antibody fragment is selected from the group consisting of: an Fv fragment, an Fc fragment, a Fab fragment, a F(ab')$_2$ fragment, a Fab' fragment, a single chain Fv (scFv) fragment, and an scFv-Fc fragment.

In some embodiments, the antibody is a monoclonal antibody.

In some embodiments, the antibody is a chimeric, humanized, or human antibody.

In certain embodiments, the antibody is a bispecific antibody. In certain embodiments, the antibody is a trispecific antibody. In certain embodiments, the antibody is a multispecific antibody.

In some embodiments, the antibody is an affinity matured antibody. In some aspects, the antibody is an affinity matured antibody derived from an illustrative sequence provided in this disclosure.

In some embodiments, the antibody is internalized by a cell after binding.

The antibodies described herein may be useful for the treatment of a variety of diseases and conditions, including cancers, autoimmune diseases, infection, and inflammation.

In some embodiments, the at least one amino acid substitution in the CH2 domain provides an antibody that has optimal functional properties. For example, the antibody can show little or no loss of binding affinity for its target antigen compared to an antibody without the at least one amino acid substitution in the CH2 domain. In certain embodiments, the antibody can show enhanced binding compared to an antibody without the amino acid substitution in the CH2 domain.

In some embodiments, the at least one amino acid substitution in the CH2 domain provides an antibody that can be made advantageously. For example, in certain embodiments, the antibody shows advantageous properties in its methods of synthesis, discussed below. In certain embodiments, the antibody can show little or no loss in yield in production compared to an antibody without the at least one amino acid substitution in the CH2 domain. In certain embodiments, the antibody can show enhanced yield in production compared to an antibody without the at least one amino acid substitution in the CH2 domain.

In some embodiments, the at least one amino acid substitution in the CH2 domain provides an antibody that has advantageous solubility. In some embodiments, the antibody can show little or no loss in solubility compared to an antibody without the at least one amino acid substitution in the CH2 domain. In some embodiments, the antibody can show enhanced solubility compared to an antibody without the at least one amino acid substitution in the CH2 domain.

In some embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In some embodiments, the at least one amino acid substitution in the CH2 domain provides an antibody that has advantageous folding. In some embodiments, the antibody can show little or no loss in proper folding compared to an antibody without the at least one amino acid substitution in the CH2 domain. In some embodiments, the antibody can show enhanced folding compared to an antibody without the at least one amino acid substitution in the CH2 domain.

The antibody can have any antibody form recognized by those of skill in the art. The antibody can comprise a single polypeptide chain—a single heavy chain or a single light chain. The antibody can also form multimers that will be recognized by those of skill in the art including homodimers, heterodimers, homomultimers, and heteromultimers. These multimers can be linked or unlinked. Useful linkages include interchain disulfide bonds typical for antibody molecules. The multimers can also be linked by other amino acids. The antibody can be an immunoglobulin such as of any class or subclass including IgA, IgA1, IgA2, IgD, IgE, IgG, IgG1, IgG2, IgG3, IgG4 and IgM. The antibody can be of the form of any antibody fragment including Fv, Fc, Fab, and (Fab')$_2$ and scFv.

Also within the scope are post-translationally modified variants of the antibodies disclosed herein. Any of the antibodies provided herein can be post-translationally modified in any manner recognized by those of skill in the art. Typical post-translational modifications for antibodies include interchain disulfide bonding, intrachain disulfide bonding, and proteolysis. Also provided herein are other post-translationally modified antibodies having modifications such as phosphorylation, methylation, acetylation, lipidation, GPI anchoring, myristoylation and prenylation. The post-translational modification can occur during production, in vivo, in vitro or otherwise. In some embodiments, the post-translational modification can be an intentional modification by a practitioner, for instance, using the methods provided herein.

Further included within the scope are antibodies fused to further peptides or polypeptides. Exemplary fusions include, but are not limited to, e.g., a methionyl antibody in which a methionine is linked to the N-terminus of the antibody resulting from the recombinant expression, fusions for the purpose of purification (including but not limited to, to poly-histidine or affinity epitopes), fusions for the purpose of linking to other biologically active molecules, fusions with serum albumin binding peptides, and fusions with serum proteins such as serum albumin. The antibodies may comprise protease cleavage sequences, reactive groups, anti-body-binding domains (including but not limited to, FLAG or poly-His) or other affinity based sequences (including but not limited to, FLAG, poly-His, GST, etc.). The antibodies may also comprise linked molecules (including but not limited to, biotin) that improve detection (including but not limited to, GFP), purification or other features of the antibody. In certain embodiments, the antibodies comprise a C-terminal affinity sequence that facilitates purification of full length antibodies. In certain embodiments, such C-terminal affinity sequence is a poly-His sequence, e.g., a 6-His sequence.

Also provided herein are antibodies having at least one amino acid substitution in the CH2 domain of the heavy chain that are conjugated to one or more conjugation moieties. The conjugation moiety can be any conjugation moiety deemed useful to one of skill in the art. For instance, the conjugation moiety can be a polymer, such as polyethylene glycol, that can improve the stability of the antibody in vitro or in vivo. The conjugation moiety can have therapeutic activity, thereby yielding an antibody-drug conjugate. The conjugation moiety can be a molecular payload that is harmful to target cells. The conjugation moiety can be a label useful for detection or diagnosis. In some embodiments, the conjugation moiety is linked to the antibody via a direct covalent bond. In some embodiments, the conjugation moiety is linked to the antibody via a linker. In some embodiments, the conjugation moiety or the linker can be attached via a non-natural amino acid introduced into the antibody. Methods of introducing a non-natural amino acid into an antibody are described, for example, in U.S. Patent Publication No. 2015-0017187 A1, which is incorporated herein by reference in its entirety. Exemplary conjugation moieties and linkers are also described in U.S. Patent Publication No. 2015-001787 A1.

Thermostability

In some embodiments, the antibody is characterized by particular thermostability parameters. As described in Example 1, the thermostability of an antibody can be characterized by measuring its melting temperatures. The melting temperatures include TM1 and TM2. TM1 represents the melting of the Fc domain of an IgG, while TM2 represents the melting of the Fab domain of an IgG.

In some embodiments, the TM2 of the antibody is at least 75° C., 75.5° C., 76° C., 76.5° C., 77° C., 77.5° C., 78° C., 78.5° C., or 79° C. In some embodiments, the TM2 of the antibody is between about 75° C. and about 80° C. In some embodiments, the TM2 of the antibody is between about 76° C. and about 79° C. In some embodiments, the TM2 of the antibody is between about 77° C. and about 78° C. In some embodiments, the TM2 of the antibody is about 75.7° C., 75.8° C., 75.9° C., 76° C., 76.1° C., 76.2° C., 76.3° C., 76.4° C., 76.5° C., 76.6° C., 76.7° C., 76.8° C., 76.9° C., 77° C., 77.1° C. or 77.2° C. In some aspects, the TM2 values described above are for aglycosylated versions of the antibody. In some aspects, the TM2 values described above are for mutated and aglycosylated versions of the antibody. In some aspects, the TM2 values described above are for amino acid-substituted and aglycosylated versions of the antibody.

In some embodiments, the TM1 of the antibody is between about 59° C. and about 62.2° C. In some embodiments, the TM1 of the antibody is less than 62.2° C. In some embodiments, the TM1 of the antibody is less than 61° C. In some embodiments, the TM1 of the antibody is less than 60° C. In some embodiments, the TM1 of the antibody is about 59° C., 59.1° C., 59.2° C., 59.3° C., 59.4° C., 59.5° C., 59.6° C., 59.7° C., 59.8° C., 59.9° C. or 60° C. In some aspects, the TM1 values described above are for aglycosylated versions of the antibody. In some aspects, the TM1 values described above are for mutated and aglycosylated versions of the antibody. In some aspects, the TM1 values described above are for amino acid-substituted and aglycosylated versions of the antibody.

Affinity

In some embodiments, the affinity of the antibody for an antigen, as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-9}$ M and $10^{-11}$ M. In some embodiments, the affinity of the antibody is between about $10^{-10}$ M and $10^{-11}$ M. In some aspects, the $K_D$ is determined at 25° C.

In some embodiments the antibody has a $k_a$ of at least about $10^5$ $M^{-1} \times sec^{-1}$. In some embodiments the antibody has a $k_a$ of at least about $10^6$ $M^{-1} \times sec^{-1}$. In some embodiments the antibody has a $k_a$ of between about $10^5$ $M^{-1} \times sec^{-1}$ and about $10^6$ $M^{-1} \times sec^{-1}$. In some aspects, the $k_a$ is determined at 25° C.

In some embodiments the antibody has a $k_d$ of about $10^{-4}$ $sec^{-1}$ or less. In some embodiments the antibody has a $k_d$ of about $10^{-5}$ $sec^{-1}$ or less. In some embodiments the antibody has a $k_d$ of between about $10^{-4}$ $sec^{-1}$ and about $10^{-5}$ $sec^{-1}$. In some aspects, the $k_d$ is determined at 25° C.

IC$_{50}$ in Drug-Conjugated Secondary Antibody Assay

In some embodiments, the antibody has an IC$_{50}$ in a drug-conjugated secondary antibody cell killing assay. Drug-conjugated secondary antibody cell killing assays are described, for example, in WO 2016/014434. In some embodiments, the IC$_{50}$ is from about 0.001 to about 1 nM. In some aspects, the IC$_{50}$ is from about 0.001 to about 0.5 nM. In some aspects, the IC$_{50}$ is from about 0.001 to about 0.25 nM. In some aspects, the IC$_{50}$ is from about 0.001 to about 0.1 nM. In some aspects, the IC$_{50}$ is from about 0.001 to about 0.05 nM. In some aspects, the IC$_{50}$ is from about 0.001 to about 0.025 nM. In some aspects, the IC$_{50}$ is from about 0.001 to about 0.009 nM. In some aspects, the IC$_{50}$ is from about 0.001 to about 0.005 nM.

Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.*, 1991, 9:457-492.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.*, 1986, 83:7059-7063; Hellstrom et al., *Proc. Natl. Acad. Sci. U.S.A.*, 1985, 82:1499-1502; and Bruggemann et al., *J. Exp. Med.*, 1987, 166:1351-1361. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.*, 1998, 95:652-656.

C1q binding assays may also be carried out to confirm that the antibody is unable to bind C1q and hence lacks CDC activity. Examples of C1q binding assays include those described in WO 2006/029879 and WO 2005/100402.

Complement activation assays include those described, for example, in Gazzano-Santoro et al., *J. Immunol. Methods*, 1996, 202:163-171; Cragg et al., *Blood*, 2003, 101: 1045-1052; and Cragg and Glennie, *Blood*, 2004, 103:2738-2743.

FcRn binding and in vivo clearance (half-life determination) can also be measured, for example, using the methods described in Petkova et al., *Intl. Immunol.*, 2006, 18:1759-1769.

Parent Antibody

The parent antibody in which the at least one amino acid substitution in the CH2 domain is made can be any antibody known to those of skill in the art, or later discovered, without limitation. The parent antibody can be substantially encoded by an antibody gene or antibody genes from any organism, including but not limited to humans, mice, rats, rabbits, camels, llamas, dromedaries, monkeys, particularly mammals and particularly human and particularly mice and rats. In some embodiments, the parent antibody may be fully human, obtained for example from a patient or subject, by using transgenic mice or other animals (Bruggemann & Taussig, 1997, *Curr. Opin. Biotechnol.* 8:455-458) or human antibody libraries coupled with selection methods (Griffiths & Duncan, 1998, *Curr. Opin. Biotechnol.* 9:102-108). The parent antibody can be from any source, including artificial or naturally occurring. For example parent antibody can be an engineered antibody, including but not limited to chimeric antibodies and humanized antibodies (Clark, 2000, *Immunol. Today* 21:397-402) or derived from a combinatorial library. In addition, the parent antibody can be an engineered variant of an antibody that is substantially encoded by one or more natural antibody genes. For example, in one embodiment the parent antibody is an antibody that has been identified by affinity maturation.

The parent antibody can have affinity to any antigen known to those of skill in the art, or later discovered. Virtually any substance may be an antigen for a parent antibody, or an antibody of the present description. Examples of useful antigens include, but are not limited to, alpha-1 antitrypsin, angiostatin, antihemolytic factor, antibodies, apolipoprotein, apoprotein, atrial natriuretic factor, atrial natriuretic polypeptide, atrial peptides, C—X—C chemokines (e.g., T39765, NAP-2, ENA-78, Gro-a, Gro-b, Gro-c, IP-10, GCP-2, NAP-4, SDF-1, PF4, MIG), calcitonin, CC chemokines (e.g., monocyte chemoattractant protein-1, monocyte chemoattractant protein-2, monocyte chemoattractant protein-3, monocyte inflammatory protein-1 alpha, monocyte inflammatory protein-1 beta, RANTES, I309, R83915, R91733, HCC1, T58847, D31065, T64262), CD40 ligand, C-kit ligand, collagen, colony stimulating factor (CSF), complement factor 5a, complement inhibitor, complement receptor 1, cytokines, (e.g., epithelial neutrophil activating peptide-78, GRO/MGSA, GRO, GRO, MIP-1, MIP-1, MCP-1), epidermal growth factor (EGF), erythropoietin ("EPO"), exfoliating toxins A and B, factor IX, factor VII, factor VIII, factor X, fibroblast growth factor (FGF), fibrinogen, fibronectin, G-CSF, GM-CSF, glucocerebrosidase, gonadotropin, growth factors, hedgehog proteins (e.g., Sonic, Indian, Desert), hemoglobin, hepatocyte growth factor (HGF), hirudin, human serum albumin, insulin, insulin-like growth factor (IGF), interferons (e.g., IFN-α, IFN-β, IFN-γ, IFN-ε, IFN-κ, IFN-ω), interleukins (e.g., IL-1, IL-2, IL-3, IL-4, IL-5, IL-6, IL-7, IL-8, IL-9, IL-10, IL-11, IL-12, etc.), keratinocyte growth factor (KGF), lactoferrin, leukemia inhibitory factor, luciferase, neurturin, neutrophil inhibitory factor (NIF), oncostatin M, osteogenic protein, parathyroid hormone, PD-ECSF, PDGF, peptide hormones (e.g., human growth hormone), pleiotropin, protein A, protein G, pyrogenic exotoxins A, B, and C, relaxin, renin, SCF, soluble complement receptor I, soluble I-CAM 1, soluble interleukin receptors (IL-1, 2, 3, 4, 5, 6, 7, 9, 10, 11, 12, 13, 14, 15), soluble TNF receptor, somatomedin, somatostatin, somatotropin, streptokinase, superantigens, i.e., staphylococcal enterotoxins (SEA, SEB, SEC1, SEC2, SEC3, SED, SEE), superoxide dismutase, toxic shock syndrome toxin (TSST-1), thymosin alpha 1, tissue plasminogen activator, tumor necrosis factor (TNFβ), tumor necrosis factor receptor (TNFR), tumor necrosis factor-alpha (TNFα), vascular endothelial growth factor (VEGF), urokinase and others. These antigens can be obtained by methods known to those of skill in the art, for example, from commercial sources or from published polypeptide or polynucleotide sequences (e.g. Genbank).

Additional antigens include, but are not limited to, transcriptional and expression activators. Exemplary transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Antigens include, but are not limited to, expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Vaccine proteins may be antigens including, but not limited to, proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Antigens may be enzymes including, but not limited to, amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase may also be antigens.

For example, the antigen may be a disease-associated molecule, such as tumor surface antigen such as B-cell idiotypes, CD20 on malignant B cells, CD33 on leukemic blasts, and HER2/neu on breast cancer. Alternatively, the antigen may be a growth factor receptor. Examples of the growth factors include, but are not limited to, epidermal growth factors (EGFs), transferrin, insulin-like growth factor, transforming growth factors (TGFs), interleukin-1, and interleukin-2. For example, a high expression of EGF receptors has been found in a wide variety of human epithelial primary tumors. TGF-α has been found to mediate an autocrine stimulation pathway in cancer cells. Several murine monoclonal antibodies have been demonstrated to be able to bind EGF receptors, block the binding of ligand to EGF receptors, and inhibit proliferation of a variety of human cancer cell lines in culture and in xenograft models. Mendelsohn and Baselga (1995) Antibodies to growth factors and receptors, in Biologic Therapy of Cancer, 2nd Ed., J B Lippincott, Philadelphia, pp 607-623. Thus, antibodies of the invention may be used to treat a variety of cancers.

The antigen may also be cell surface protein or receptor associated with coronary artery disease such as platelet glycoprotein IIb/IIIa receptor, autoimmune diseases such as CD4, CAMPATH-1 and lipid A region of the gram-negative bacterial lipopolysaccharide. Humanized antibodies against CD4 have been tested in clinical trials in the treatment of patients with mycosis fungoides, generalized postular psoriasis, severe psoriasis, and rheumatoid arthritis. Antibodies against lipid A region of the gram-negative bacterial lipopolysaccharide have been tested clinically in the treatment of septic shock. Antibodies against CAMPATH-1 have also been tested clinically in the treatment of against refractory rheumatoid arthritis. Thus, antibodies provided herein may be used to treat a variety of autoimmune diseases.

Useful antigens also include proteins or peptides associated with human allergic diseases, such as inflammatory mediator proteins, e.g. interleukin-1 (IL-1), tumor necrosis factor (TNF), leukotriene receptor and 5-lipoxygenase, and adhesion molecules such as V-CAM/VLA-4. In addition, IgE may also serve as the antigen because IgE plays pivotal role in type I immediate hypersensitivity allergic reactions such as asthma. Studies have shown that the level of total serum IgE tends to correlate with severity of diseases, especially in asthma. Burrows et al. (1989) "Association of asthma with serum IgE levels and skin-test reactivity to allergens" *New Engl. J. Med.* 320:271-277. Thus, Antibodies selected against IgE may be used to reduce the level of IgE or block the binding of IgE to mast cells and basophils in the treatment of allergic diseases without having substantial impact on normal immune functions.

The antigen can also be a viral surface or core protein which may serve as an antigen to trigger immune response of the infected host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

The antigen can also be a mutated tumor suppressor gene product that has lost its tumor-suppressing function and may render the cells more susceptible to cancer. Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2. DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. p53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. Thus, Antibodies may be used to block the interactions of the gene product with other proteins or biochemicals in the pathways of tumor onset and development.

The antigen may be a CD molecule including but not limited to, CD1a, CD1b, CD1c, CD1d, CD2, CD3γ, CD3δ, CD3ε, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79α, CD79β, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD110-113, CD114, CD115, CD116, CD117, CD118, CD119, CD120a, CD120b, CD121a, CD121b, CD122, CD123, CDw124, CD125, CD126, CDw127, CDw128a, CDw128b, CD129, CDw130, CD131, CD132, CD133, CD134, CD135, CD136, CDw137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCRζ. The antigen may be VEGF, VEGF receptor, EGFR, Her2, TNFa, TNFRI receptor, GPIIb/IIIa, IL-2Rα chain, IL-2Rβ chain, RSV F protein, alpha-4 integrin, IgE, IgE receptor, digoxin, carpet viper venom, complement C5, OPGL, CA-125 tumor antigen, Staphylococci proteins, *Staphylococcus epidermidis* proteins, *Staphylococcus aureus* proteins, proteins involved Staphylococcal infection (including but not limited to, *Staphylococcus aureus* and *Staphylococcus epidermidis*), IL-6 receptor, CTLA-4, RSV, Tac subunit of IL-2 receptor, IL-5, and EpCam. The antigen may be a fragment of a molecule.

Parent antibodies can be any antibody known in the art or any antibody discovered or developed by those of skill in the art without limitation. Examples include, but are not limited to anti-TNF antibody (U.S. Pat. No. 6,258,562), anti-IL-12 and/or anti-IL-12p40 antibody (U.S. Pat. No. 6,914,128); anti-IL-18 antibody (U.S. Patent Publication No. 2005/0147610), anti-05, anti-CBL, anti-CD147, anti-gp120, anti-VLA-4, anti-CD11a, anti-CD18, anti-VEGF, anti-CD40L, anti CD-40 (e.g., see PCT Publication No. WO 2007/124299) anti-Id, anti-ICAM-1, anti-CXCL13, anti-CD2, anti-EGFR, anti-TGF-β2, anti-HGF, anti-cMet, anti DLL-4, anti-NPR1, anti-PLGF, anti-ErbB3, anti-E-selectin, anti-Fact VII, anti-Her2/neu, anti-F gp, anti-CD11/18, anti-CD14, anti-ICAM-3, anti-RON, anti-SOST, anti CD-19, anti-CD80 (e.g., see PCT Publication No. WO 2003/039486, anti-CD4, anti-CD3, anti-CD23, anti-β2-integrin, anti-α4β7, anti-CD52, anti-HLA DR, anti-CD22 (e.g., see U.S. Pat. No. 5,789,554), anti-CD20, anti-MIF, anti-CD64 (FcR), anti-TCR α and/or β, anti-CD2, anti-Hep B, anti-CA 125, anti-EpCAM, anti-gp120, anti-CMV, anti-gpIIbIIIa, anti-IgE, anti-CD25, anti-CD33, anti-CD74, anti-PD1, anti-LAG3, anti-TIM3, anti-Folate receptor alpha antibody, anti-5T4 antibody, anti-BCMA, anti-ROR1, anti-HLA, anti-IGF1,2, anti IGFR, anti-VNRintegrin, anti-IL-1α, anti-IL-1β, anti-IL-1 receptor, anti-IL-2 receptor, anti-IL-4, anti-IL-4 receptor, anti-IL5, anti-IL-5 receptor, anti-IL-6, anti-IL-8, anti-IL-9, anti-IL-13, anti-IL-13 receptor, anti-IL-17, anti-IL-6R, anti-RANKL, anti-NGF, anti-DKK, anti-αVβ3, anti-IL-17A, anti-IL23p19 and anti-IL-23 (see Presta, L. G. (2005) *J. Allergy Clin. Immunol.* 116:731-6 and those described in Ecker, et al., 2015, *MAbs* 7(1):9-14.

Parent antibodies can also be selected from various therapeutic antibodies approved for use, in clinical trials, or in development for clinical use. Such therapeutic antibodies include, but are not limited to, rituximab (Rituxan®, IDEC/Genentech/Roche) (see, for example, U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT Application No. PCT/US2003/040426), trastuzumab (Herceptin®, Genentech) (see, for example, U.S. Pat. No. 5,677,171), a humanized anti-Her2/neu antibody approved to treat breast cancer; pertuzumab (rhuMab-2C4, Omnitarg®), currently being developed by Genentech; an anti-Her2 antibody (U.S. Pat. No. 4,753,894; cetuximab (Erbitux®, Imclone) (U.S. Pat. No. 4,943,533; PCT Publication No. WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Pat. No. 7,247,301), currently being developed by Genmab; 425, EMD55900, EMD62000, and EMD72000 (Merck KGaA) (U.S. Pat. No. 5,558,864; Murthy, et al. (1987) *Arch. Biochem. Biophys.* 252(2): 549-60; Rodeck, et al. (1987) *J. Cell. Biochem.* 35(4): 315-20; Kettleborough, et al. (1991) *Protein Eng.* 4(7): 773-83; ICR62 (Institute of Cancer Research) (PCT Publication No. WO 95/20045; Modjtahedi, et al. (1993) *J. Cell. Biophys.* 22(I-3): 129-46; Modjtahedi, et al. (1993) *Br. J. Cancer* 67(2): 247-53; Modjtahedi, et al. (1996) *Br. J. Cancer* 73(2): 228-35; Modjtahedi, et al. (2003) *Int. J. Cancer* 105(2): 273-80); TheraCIM hR3 (YM Biosciences, Canada and Centro de Immunologia Molecular, Cuba (U.S. Pat. Nos. 5,891,996; 6,506,883; Mateo, et al. (1997) Immunotechnol. 3(1): 71-81); mAb-806 (Ludwig Institute for Cancer Research, Memorial Sloan-Kettering) (Jungbluth, et al. (2003) *Proc. Natl. Acad. Sci. USA.* 100(2): 639-44); KSB-102 (KS Biomedix); MR1-1 (IVAX, National Cancer Institute) (PCT Publication No. WO 01/62931A2); and SC100 (Scancell) (PCT Publication No. WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFα antibody developed by Centocor, adalimumab (Humira®), an anti-TNFα antibody developed by Abbott, Humicade®, an anti-TNFα antibody developed by Celltech, golimumab (CNTO-148), a fully human TNF antibody developed by Centocor, etanercept (Enbrel®), an p75 TNF receptor Fc fusion developed by Immunex/Amgen, lenercept, an p55TNF receptor Fc fusion previously developed by Roche, ABX-CBL, an anti-CD147 antibody being developed by Abgenix, ABX-1L8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-α-4-β-1 (VLA-4) and α-4-β-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β antibody being developed by Cambridge Antibody Technology, ABT 874 (J695), an anti-IL-12 p40 antibody being developed by Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B® an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD 23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (Iabetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-β2 integrin antibody being developed by Xoma. In another embodiment, the therapeutics include KRN330 (Kirin); huA33 antibody (A33, Ludwig Institute for Cancer Research); CNTO 95 (alpha V integrins, Centocor); MEDI-522 (αVβ3 integrin, Medimmune); volociximab (αVβ1 integrin, Biogen/PDL); Human mAb 216 (B cell glycosolated epitope, NC1); BiTE MT103 (bispecific CD19×CD3, Medimmune); 4G7×H22 (Bispecific Bcell×FcγR1, Medarex/Merck KGa); rM28 (Bispecific CD28×MAPG, EP Patent No. EP1444268); MDX447 (EMD 82633) (Bispecific CD64×EGFR, Medarex); Catumaxomab (removab) (Bispecific EpCAM×anti-CD3, Trion/Fres); Ertumaxomab (bispecific HER2/CD3, Fresenius Biotech); oregovomab (OvaRex) (CA-125, ViRexx); Rencarex® (WX G250) (carbonic anhydrase IX, Wilex); CNTO 888 (CCL2, Centocor); TRC105 (CD105 (endoglin), Tracon); BMS-663513 (CD137 agonist, Brystol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NC1); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD122 (CD40, Novartis); SGN-40 (CD40, Seattle Genentics); Campath1h (Alemtuzumab) (CD52, Genzyme); MDX-1411 (CD70, Medarex); hLL1 (EPB-1) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675,2) (CTLA4, Pfizer); HGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam, Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DRβ chain, PDL Pharma); AMG-479 (IGF-1R, Amgen); anti-IGF-1R R1507 (IGF1-R, Roche); CP 751871 (IGF1-R, Pfizer); IMC-A12 (IGF1-R, Imclone); BIIB022 (IGF-1R, Biogen); Mik-β-1 (IL-2Rb (CD122), Hoffman LaRoche); CNTO 328 (IL6, Centocor); Anti-KIR (1-7F9) (Killer cell Ig-like Receptor (KIR), Novo); Hu3S193 (Lewis (y), Wyeth, Ludwig Institute of Cancer Research); hCBE-11 (LTβR, Biogen); HuHMFG1 (MUC1, Antisoma/NC1); RAV12 (N-linked carbohydrate epitope, Raven); CAL (parathyroid hormone-related protein (PTH-rP), University of California); CT-011 (PD1, CureTech); MDX-1106 (ono-4538) (PD1, Medarex/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNFa, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab, PCT Publication No. WO/2000/034337, University of Texas); IMC-18F1 (VEGFR1, Imclone); IMC-1121 (VEGFR2, Imclone).

In some embodiments, the parent antibody is a bi-specific antibody having two different antigen-binding arms that bind to independent targets. Dual-target bi-specific antibodies are known in the art, however, the parent antibody can also be any dual-target bi-specific antibody as long as at least one arm comprises a CH2 region. For example, in some embodiments, the bi-specific antibody can include two independent antigen-binding polypeptide constructs or antigen binding domains, wherein at least one polypeptide construct specifically binds to a first target and at least one polypeptide construct specifically binds to a second target. The first antigen-binding polypeptide construct and second antigen-binding polypeptide construct can independently comprise a structure selected from the group of: an scFvFc and a FabFc. The first and second antigen-binding polypeptide constructs can consist of the same format or different formats from each other. For example, in some embodiments, the first antigen-binding polypeptide construct comprises an scFvFc and the second antigen binding antigen-binding polypeptide construct comprises a FabFc. In some embodiments, the first and second antigen-binding polypeptide constructs each comprise an scFvFc directed to independent targets. In some embodiments, the first and second antigen binding polypeptide constructs each each comprise a FabFc directed to independent targets. Any combination of antibody formats suitable for the bi-specific antibody constructs can be used to produce a variant as disclosed herein.

Examples of useful bispecific parent antibodies include, but are not limited to, those with one antibody directed against a tumor cell antigen and the other antibody directed against a cytotoxic trigger molecule such as anti-FcγRI/anti-CD 15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific antibodies with one antibody which binds specifically to a tumor antigen and another antibody which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; bispecific antibodies for converting enzyme activated prodrugs such as anti-CD30/anti-alkaline phosphatase (which catalyzes conversion of mitomycin phosphate prodrug to mitomycin alcohol); bispecific antibodies which can be used as fibrinolytic agents such as anti-fibrin/anti-tissue plasminogen activator (tPA), anti-fibrin/anti-urokinase-type plasminogen activator (uPA); bispecific antibodies for targeting immune complexes to cell surface receptors such as anti-low density lipoprotein (LDL)/anti-Fc receptor (e.g. FcγRI, FcγRII or FcγRIII); bispecific antibodies for use in therapy of infectious diseases such as anti-CD3/anti-herpes simplex virus (HSV), anti-T-cell receptor: CD3 complex/anti-influenza, anti-FcγR/anti-HIV; bispecific antibodies for tumor detection in vitro or in vivo such as anti-CEA/anti-EOTUBE, anti-CEA/anti-DPTA, anti-anti-p185$^{HER2}$/anti-hapten; bispecific antibodies as vaccine adjuvants (see Fanger, M. W. et al., *Crit Rev Immunol.* 1992; 12(34):101-24, which is incorporated by reference herein); and bispecific antibodies as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan, O et R. O'Kennedy, Biochim Biophys Acta. 1990 Aug. 1; 1040 (1):1-11, which is incorporated by reference herein). Examples of trispecific antibodies include anti-CD3/anti-CD4/anti-CD37, anti-CD3/anti-CD5/anti-CD37 and anti-CD3/anti-CD8/anti-CD37. In some embodiments, the antibody is a multispecific antibody.

Linkers and Payloads

Also provided herein are antibody conjugates comprising an antibody as disclosed herein linked or connected to a payload moiety. In some embodiments, the antibody can be linked to any payload moiety or molecular entity capable of forming a covalent bond to a natural or non-natural amino acid in the antibody, directly or indirectly via a linker. In some embodiments, the linker is a cleavable linker. In some embodiments, the linker is a non-cleavable linker.

In some embodiments, the linker is any divalent or multivalent linker known to those of skill in the art. Generally, the linker is capable of forming covalent bonds to the functional moiety R and the alpha carbon of a natural or non-natural amino acid. Useful divalent linkers a bond, alkylene, substituted alkylene, heteroalkylene, substituted heteroalkylene, arylene, substituted arylene, heteroarlyene and substituted heteroarylene. In certain embodiments, the linker is $C_{1-10}$ alkylene or $C_{1-10}$ heteroalkylene.

The payload can be any molecular entity that one of skill in the art might desire to conjugate to the antibody. In certain embodiments, the payload is a therapeutic moiety. In such embodiment, the antibody conjugate can be used to target the therapeutic moiety to its molecular target. In certain embodiments, the payload is a labeling moiety. In such embodiments, the antibody conjugate can be used to detect binding of the antibody to its target. In certain embodiments, the payload is a cytotoxic moiety. In such embodiments, the conjugate can be used target the cytotoxic moiety to a diseased cell, for example a cancer cell, to initiate destruction or elimination of the cell. Conjugates comprising other molecular payloads apparent to those of skill in the art are within the scope of the conjugates described herein.

In certain embodiments, a conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof.

Suitable linkers and payloads are described, for example, in U.S. 2015-0017187 A1, which is incorporated herein by reference in its entirety.

Preparation of Antibodies

Antigen Preparation

An antigen to be used for production of antibodies may be an intact antigen or a fragment of the antigen. Other antigen forms useful for generating antibodies will be apparent to those skilled in the art.

Monoclonal Antibodies

Monoclonal antibodies may be obtained, for example, using the hybridoma method first described by Kohler et al., *Nature,* 1975, 256:495-497, and/or by recombinant DNA methods (see e.g., U.S. Pat. No. 4,816,567). Monoclonal antibodies may also be obtained, for example, using phage or yeast-based libraries. See e.g., U.S. Pat. Nos. 8,258,082 and 8,691,730.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, Calif.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

Humanized Antibodies

Humanized antibodies may be generated by replacing most, or all, of the structural portions of a monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J. Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370.

Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589,369 and 5,545,807. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573,905). Human antibodies may also be generated by in vitro activated B cells (see e.g., U.S. Pat. Nos. 5,567,610 and 5,229,275). Human antibodies may also be derived from yeast-based libraries (see e.g., U.S. Pat. No. 8,691,730).

Vectors, Host Cells, and Recombinant Methods

The invention also provides isolated nucleic acids encoding anti-CD74 antibodies, vectors and host cells comprising the nucleic acids, and recombinant techniques for the production of the antibodies.

For recombinant production of the antibody, the nucleic acid encoding it may be isolated and inserted into a replicable vector for further cloning (i.e., amplification of the DNA) or expression. In some aspects, the nucleic acid may be produced by homologous recombination, for example as described in U.S. Pat. No. 5,204,244.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615.

Illustrative examples of suitable host cells are provided below. these host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter*, *Erwinia*, *Klebsiella*, *Proteus*, *Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-CD74 antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe*, *Kluyveromyces* (*K. lactis*, *K. fragilis*, *K. bulgaricus K. wickeramii*, *K. waltii*, *K. drosophilarum*, *K. thermotolerans*, and *K. marxianus*), *Yarrowia*, *Pichia pastoris*, *Candida* (*C. albicans*), *Trichoderma reesia*, *Neurospora crassa*, *Schwanniomyces* (*S. occidentalis*), and filamentous fungi such as, for example *Penicillium*, *Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-CD74 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13). Protein G is useful for all mouse isotypes and for human γ3 (Guss et al., *EMKO J.*, 1986, 5:1567-1575).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5-4.5, generally performed at low salt concentrations (e.g., from about 0-0.25 M salt).

Pharmaceutical Compositions and Methods of Administration

The antibodies and antibody conjugates provided herein can be formulated into pharmaceutical compositions using methods available in the art and those disclosed herein. Any of the antibodies provided herein can be provided in the appropriate pharmaceutical composition and be administered by a suitable route of administration.

The methods provided herein encompass administering pharmaceutical compositions comprising at least one antibody or antibody conjugate provided herein and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions, antibodies, or antibody conjugates provided herein may be administered by any route known in the art. In certain embodiments, a pharmaceutical composition or antibody provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, antibodies are supplied as a water free concentrate. In some embodiments, the antibody is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

In another embodiment, the pharmaceutical composition is supplied in liquid form. In some embodiments, the pharmaceutical composition is provided in liquid form and is substantially free of surfactants and/or inorganic salts. In some embodiments, the antibody is supplied as in liquid form at a unit dosage of at least 0.1 mg/ml, at least 0.5 mg/ml, at least 1 mg/ml, at least 2.5 mg/ml, at least 3 mg/ml, at least 5 mg/ml, at least 8 mg/ml, at least 10 mg/ml, at least 15 mg/ml, at least 25 mg/ml, at least 30 mg/ml, or at least 60 mg/ml.

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Further encompassed herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more excipients that reduce the rate by which an antibody will decompose. Such antibodies, which are referred to herein as "stabilizers," include, but are not limited to, antioxidants such as ascorbic acid, pH buffers, or salt buffers.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

Dosage and Unit Dosage Forms

In human therapeutics, the doctor will determine the posology which he considers most appropriate according to a preventive or curative treatment and according to the age, weight, stage of the infection and other factors specific to the subject to be treated.

The amount of the antibody, antibody conjugate, or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody, antibody conjugate, or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

Therapeutic Applications

For therapeutic applications, the antibodies or antibody conjugates disclosed herein are administered to a mammal, generally a human, in a pharmaceutically acceptable dosage form such as those known in the art and those discussed above. For example, the antibodies and antibody conjugates disclosed herein may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies and antibody conjugates also are suitably administered by peritumoral, intralesional, or perilesional routes, to exert local as well as systemic therapeutic effects. The intraperitoneal route may be particularly useful, for example, in the treatment of ovarian tumors.

A therapeutically effective amount of the antibody, antibody conjugate, or composition is an amount that is effective to reduce the severity, the duration and/or the symptoms of a particular disease or condition. The amount of the antibody, antibody conjugate, or composition that will be therapeutically effective in the prevention, management, treatment and/or amelioration of a particular disease can be determined by standard clinical techniques. The precise amount of the antibody, antibody conjugate, or composition to be administered with depend, in part, on the route of administration, the seriousness of the particular disease or condition, and should be decided according to the judgment of the practitioner and each subject's circumstances.

In some embodiments, the effective amount of the antibody or antibody conjugate provided herein is between about 0.025 mg/kg and about 1000 mg/kg body weight of a human subject. In certain embodiments, the antibody is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of antibody or antibody conjugate provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

Diagnostic Applications

In some embodiments, the antibodies provided herein are used in diagnostic applications. For example, an antibody disclosed herein that is specific for a given antigen may be useful in assays for the given antigen. In some aspects the antibody can be used to detect the expression of the given antigen in various cells and tissues. These assays may be useful, for example, diagnosing cancer, infection and autoimmune disease.

In the methods, the formation of a complex between the antibody and antigen can be detected by any method known to those of skill in the art. Examples include assays that use secondary reagents for detection, ELISA's and immunoprecipitation and agglutination assays. A detailed description of these assays is, for example, given in Harlow and Lane, Antibodies: A Laboratory Manual (Cold Spring Harbor Laboratory, New York 1988 555-612, WO 96/13590 to Maertens and Stuyver, Zrein et al. (1998) and WO 96/29605.

For in situ diagnosis, the antibody may be administered to a subject by methods known in the art such as, for example, intravenous, intranasal, intraperitoneal, intracerebral, intraarterial injection such that a specific binding between the antibody and antigen may occur. The antibody/antigen complex may conveniently be detected through a label attached to the antibody or any other art-known method of detection.

In some diagnostic applications, the antibody may be labeled with a detectable moiety. Suitable detectable moieties include, but are not limited to radioisotopes, fluorescent labels, and enzyme-substrate labels. In another embodiment, the antibody need not be labeled, and the presence thereof can be detected using a labeled secondary antibody which specifically binds to the antibody disclosed herein.

Affinity Purification Reagents

The antibodies disclosed herein can be used as affinity purification agents. In this process, the antibodies can be immobilized on a solid phase such a resin or filter paper, using methods well known in the art. The immobilized antibody is contacted with a sample containing a protein (or fragment thereof) that specifically binds to the antibody and is to be purified, and thereafter the support is washed with a suitable solvent that will remove substantially all the material in the sample except the protein, which is bound to the immobilized antibody. Finally, the support is washed with another suitable solvent, such as glycine buffer, pH 5.0, that will release the bound protein from the antibody.

Kits

In some embodiments, an antibody or antibody conjugate as described herein can be provided in a kit, i.e., a packaged combination of reagents in predetermined amounts with instructions for performing a procedure. In some embodiments, the procedure is a diagnostic assay. In other embodiments, the procedure is a therapeutic procedure.

EXAMPLES

Example 1

Properties of Antibodies with Single Amino Acid Substitutions

For rational re-design of the exposed glycosylation site of the CH2 domain, a structural homology search was conducted on Ig domains with similar structure to the CH2 domain with hydrophilic residues instead of hydrophobic residues at the exposed glycosylation site. Mutations observed from IgE ("ige"), PD1 ("PD1") and shark IgNAR domains ("sh1," "sh2" and "sh3") were then cloned into trastuzumab according to standard practice. This example describes experiments designed to characterize the properties, including the thermal stability (TM) of aglycosylated trastuzumab ("TRAZ") parent antibody and the resulting variants. Parent and variant antibodies were then scaled-up and purified separately two times by affinity chromatography using Protein A Sepharose beads. Antibodies were then further characterized for thermostability, which was measured by differential scanning fluorimetry (DSF). DSF was performed after the first purification step.

A thermal shift assay was carried out by mixing the protein to be assayed (trastuzumab and variants) with an environmentally sensitive dye (SYPRO Orange, Life Technologies Cat #S-6650) in a phosphate buffered solution (PBS), and monitoring the fluorescence of the mixture in real time as it underwent controlled thermal denaturation. The final concentration of the protein in the assay mixture was between 100-250 µg/mL, and the dye was diluted 1:1000 from the original stock (stock dye is 5000× in DMSO). After dispensing 5 µL aliquots of the protein-dye mixture in a 384-well microplate (Bio-Rad Cat #MSP-3852), the plate was sealed with an optically clear sealing film (Bio-Rad Cat #MSB-1001), and placed in a 384-well plate real-time thermocycler (Bio-Rad CFX384 Real Time System). The protein-dye mixture was heated from 25° C. to 95° C., at increments of 0.1° C. per cycle (~1.5° C. per minute), allowing 3 seconds of equilibration at each temperature before taking a fluorescence measurement. At the end of the experiment, the transition melting temperatures (TM1 and TM2) were determined using the Bio-Rad CFX manager software. TM1 represents the melting temperature of the Fc domain. TM2 represents the melting temperature of the Fab domain. The TM2 for certain illustrative antibodies provided in this disclosure is approximately equal or higher than the TM2 for the parent antibody. The results for these studies are provided in Table 5.

TABLE 5

Properties of parent antibody (Trastazumab) and antibody variants

| Antibody ID | [IgG], µg/mL | TM1, ° C. | TM2, ° C. |
|---|---|---|---|
| TRAZ | 1039.2 | 59.4 | 77.1 |
| F241R | 1186.6 | 59.3 | 76.8 |
| F241S | 1199.5 | 59.4 | 76.5 |
| F241Y | 1083.1 | 59.5 | 76.8 |
| F243R | 871.6 | 55 | 76.9 |
| F243S | 893.5 | 54.7 | 76.6 |
| V262E | 1394.3 | 59.1 | 76.8 |
| V262T | 1306.0 | 55.1 | 77 |
| V264R | 1271.0 | 59.2 | 76.7 |
| V264S | 1439.1 | 59.3 | 77 |
| V303R | 1306.5 | 59.4 | 76.8 |
| V303T | 1208.6 | 60.5 | 77 |
| V305R | 1276.5 | 59.4 | 76.4 |
| V305T | 1121.8 | 59.8 | 75.5 |

As illustrated above, point mutations at V262E, V264S, V303R and V305R increased antibody yields without comprising thermostability of the antibody.

Example 2

Properties of Antibodies with Combinations of Amino Acid Substitutions

This example describes experiments designed to characterize the properties, including the thermal stability (TM)) of aglycosylated trastuzumab ("TRAZ") parent antibody and variants that contain combinations of amino acid substitutions. Mutations were cloned into trastuzumab as described in Example 1. Parent and variant antibodies were then scaled-up and purified separately in quadruplicate. Differential scanning fluorimetry (DSF) was performed with the final sample after purification. Table 6 includes the properties for the combinations of amino acid substitutions tested in this example.

TABLE 6

Properties of parent antibody (trastuzumab) and antibody variants containing combinations of amino acid substitutions.

| Antibody ID | Average Yield (μg/mL) | Standard Dev. | CV (%) | % yield relative to WT | TM1, °C. | TM2, °C. |
| --- | --- | --- | --- | --- | --- | --- |
| V262E V264S | 1643.484923 | 216.9015 | 13% | 35% | 57.1 | 75.9 |
| V262E V303R | 1692.008214 | 147.4389 | 9% | 39% | 59.2 | 76.1 |
| V262E V305R | 1524.387177 | 142.0968 | 9% | 25% | 59.3 | 75.8 |
| V264S V303R | 1598.630741 | 110.1353 | 7% | 31% | 58.8 | 75.8 |
| V264S V305R | 1601.722585 | 127.9384 | 8% | 32% | 59.1 | 75.8 |
| V303R V305R | 980.4801861 | 93.42927 | 10% | −19% | 59.3 | 75.5 |
| V262E V264S V303R | 1513.087538 | 87.96965 | 6% | 24% | 58.8 | 75.7 |
| V262E V264S V305R | 1371.915281 | 218.0797 | 16% | 13% | 59.3 | 75.8 |
| V262E V303R V305R | 1523.765047 | 37.4539 | 2% | 25% | 59.4 | 75.8 |
| V264S V303R V305R | 1244.030121 | 175.42 | 14% | 2% | 59.5 | 75.9 |
| V262E V264S V303R V305R | 1403.561608 | 96.61587 | 7% | 15% | 59.3 | 75.7 |
| WT | 1215.770334 | 188.9825 | 16% | 0% | 59.3 | 76.5 |
| V262E | 1535.457891 | 74.77478 | 5% | 26% | 59.4 | 76.3 |
| V264S | 1464.901716 | 177.5559 | 12% | 20% | 59.2 | 76.5 |
| V303R | 1338.09235 | 176.6385 | 13% | 10% | 59.2 | 75.9 |
| V305R | 834.066189 | 539.6917 | 65% | −31% | 59.2 | 75.8 |

Figure 2:
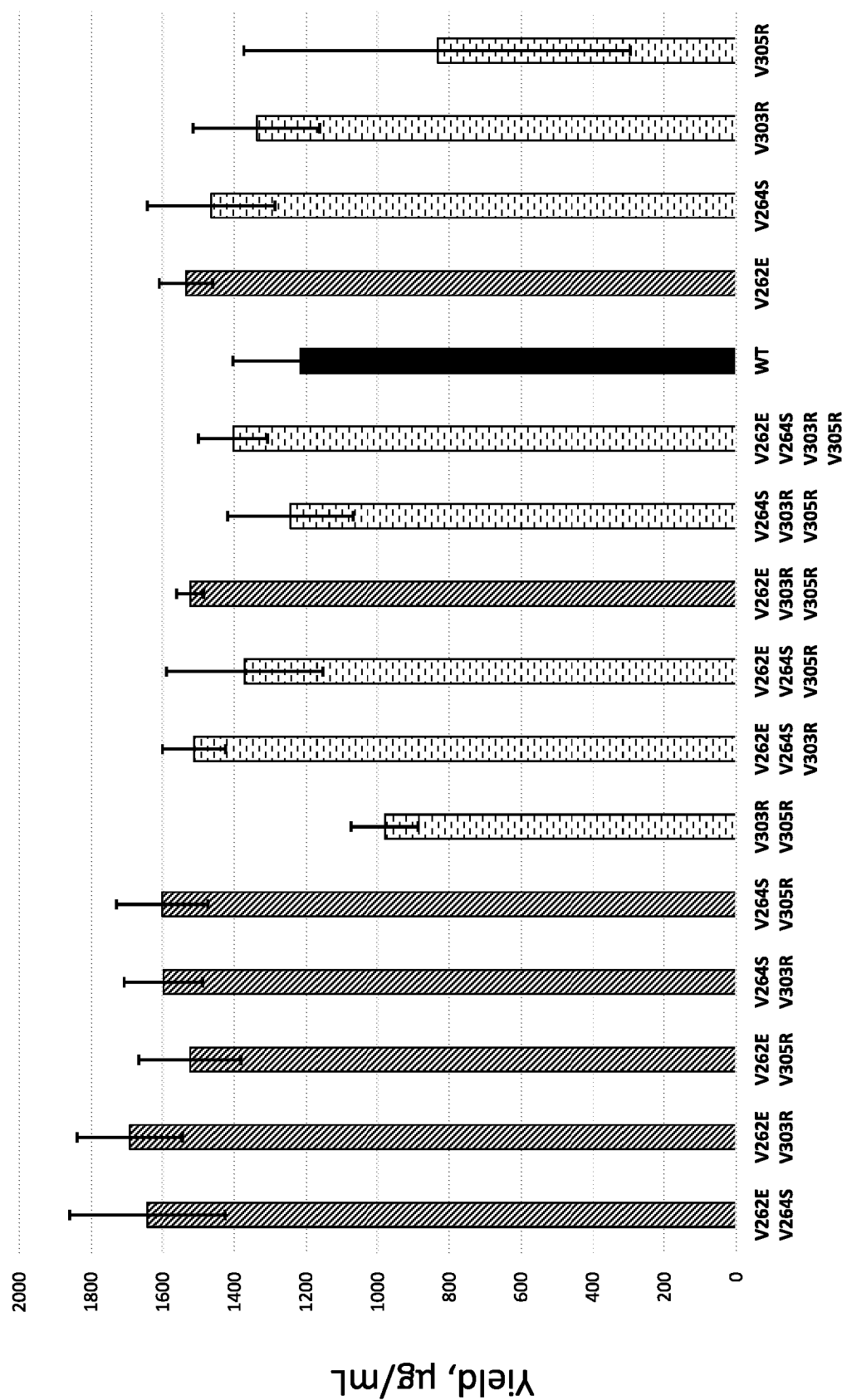
FIG. 2 is a bar chart illustrating overall yields for an exemplary parent antibody and variants having single amino acid substitutions or combinations of amino acid substitutions relative to the parent antibody.

FIG. 2 illustrates the overall yield for each combination of mutations or for each single mutation tested relative to wild-type antibody yield (or gene expression). The wild type antibody is shown with solid color, whereas mutants that demonstrated ≥25% expression relative to wild type are shown with diagonal stripe pattern.

The V262E-V303R double mutant showed a 39% increase in yield (and gene expression) relative to the wild-type Trastazumab parent antibody. In addition, this double mutant appeared to have comparable TM1 and TM2 values relative to the parent antibody.

Other double mutants that showed good potential include the V262-V305R double mutant and the V264S-V303R double mutant.

The results from this round of testing also confirm that the V262E single mutant showed potential for further testing due to its high yield relative to the parent antibody and its comparable TM1 and TM2 values. The V264S single mutant also showed good potential for further testing.

Example 3

Immunoglobulin Expression Tests

Six variants based on mutations found in shark IgNAR domains were selected based on improved expression and thermostability properties (Example 2). Table 7 lists the various mutations that were cloned into the trastuzumab and characterized.

TABLE 7

Tested variants of trastuzumab

| Antibody ID | Mutation(s) |
| --- | --- |
| 1 | Wild type (parent) |
| 2 | V262E |

TABLE 7-continued

Tested variants of trastuzumab

| Antibody ID | Mutation(s) |
| --- | --- |
| 3 | V262E V303R |
| 4 | V262E V305R |
| 5 | V262E V303R V305R |

TABLE 7-continued

Tested variants of trastuzumab

| Antibody ID | Mutation(s) |
| --- | --- |
| 6 | V264S V303R |
| 7 | V264S V305R |

Different properties of the six variants were characterized relative to the wild type parent antibody. These included solubility and assembly efficiency.

To quantify protein yield, the reaction mixture was supplemented with a small amount of $^{14}C$ labeled leucine (3 μL per 100 μL reaction, PerkinElmer: NEC279E001MC, 0.1 mCi/mL). A 4 μL aliquot of each reaction was spotted on a Filtermat A (PerkinElmer: 1450-421) before and after centrifugation at 6,100×g for 10 minutes and dried on a hot plate at 100° C. for 10 minutes. The Filtermats with centrifuged and non-centrifuged samples were washed three times for 15 minutes with 5% trichloroacetic acid on ice to remove unincorporated $^{14}C$ leucine, rinsed with absolute ethanol and dried on the hot plate. Additional Filtermat with non-centrifuged samples was not washed. All Filtermats were coated with MeltiLex melt-in scintillate (PerkinElmer: 1450-441) and counted in a Wallac MicrobetaTrilux liquid scintillation and luminescence counter (model 1450). Total and soluble protein yields were calculated according to:

$$P_{tot} = [Leu]_{total} \times \frac{MW}{(\# \ Leu)} \times \frac{C_{tot}}{C_{full}}$$

$$P_{sol} = [Leu]_{total} \times \frac{MW}{(\# \ Leu)} \times \frac{C_{sol}}{C_{full}}$$

where $P_{tot}$ and $P_{sol}$ are the total and soluble protein yield in mg/mK, $[Leu]_{total}$ is the total leucine concentration in the reaction (commonly 2 mM), MW/(# Leu) is the ratio of molecular weight to number of leucine residues in the proteins, $C_{tot}/C_{full}$ is the ratio of counts measured by the scintillation counter in the total synthesized fraction with TCA wash and full reaction mixture without TCA wash, and $C_{sol}/C_{full}$ is the ratio of counts measured by the scintillation counter in the soluble fraction and full reaction mixture. The solubility is the ratio of $P_{sol}$ to $P_{tot}$.

For products with quaternary structure (Fab, scFvFc, IgG), autoradiograms were run using 4-12% Bis-Tris SDS-PAGE gels (Invitrogen) to determine assembly of the proper complex. Both reducing and non-reducing gels were run following the manufacturer's instructions. Exposed phosphor screens were scanned by Typhoon FLA 7000 (GE Healthcare life sciences) and the intensity of the bands was quantified by ImageQuant software (GE). The final yield of assembled complex was calculated according to the equation:

$$P_{complex} = P_{sol} \times I_{nr}^{complex} / \Sigma I_r$$

where $P_{comlex}$ is the yield of the correctly assembled complex in mg/mL, $P_{sol}$ is the soluble protein yield, $I_{nr}^{complex}$ is the intensity of the correctly assembled complex band on the non-reducing gel, and $\Sigma I_r$ is the sum of intensities of all bands on the reducing gel. $I_{nr}^{complex}/\Sigma I_r$ is defined as assembly efficiency.

Figure 3:
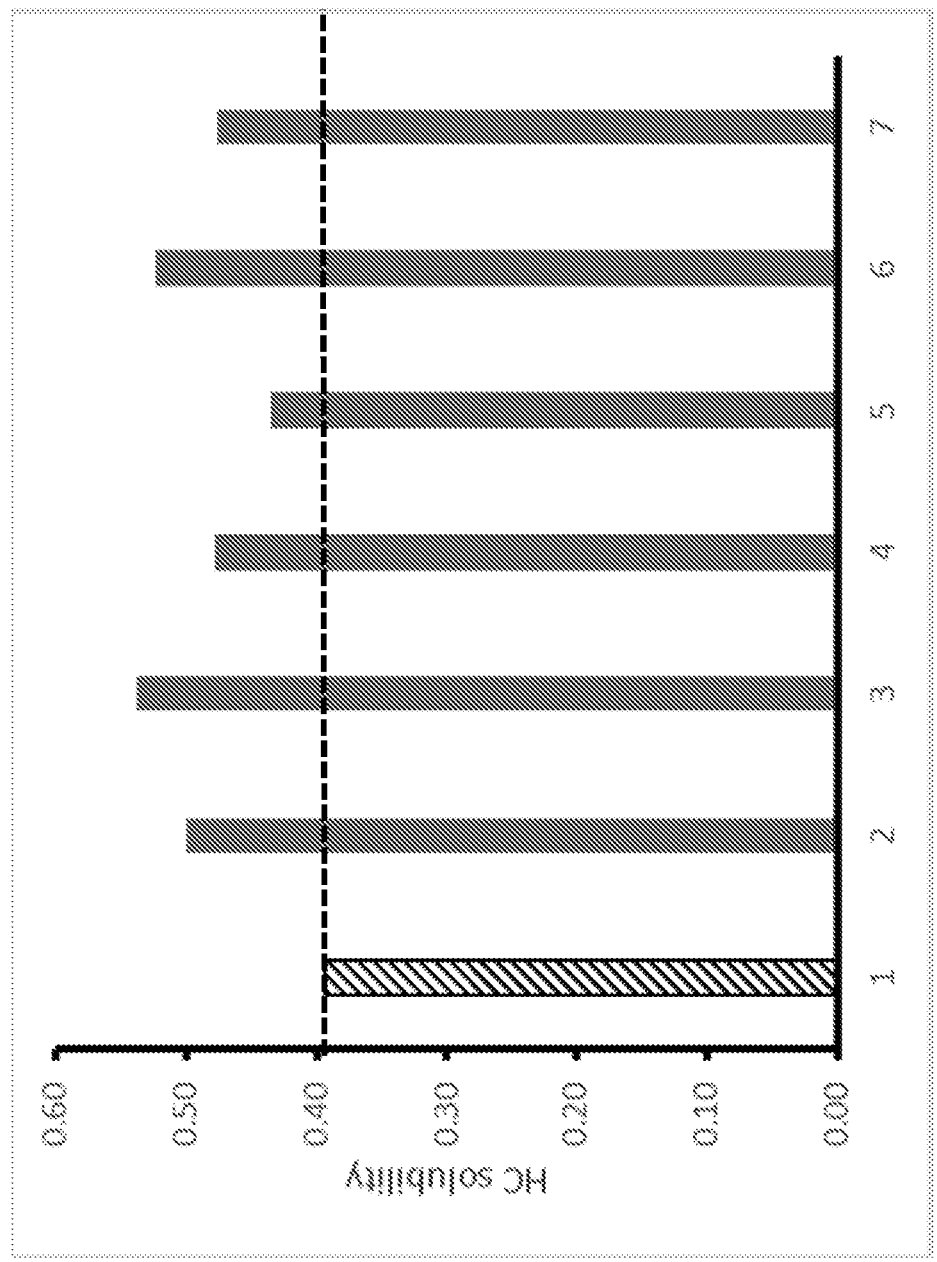
FIG. 3 is a bar chart illustrating solubility for an exemplary parent antibody and variants having single amino acid substitutions or combinations of amino acid substitutions relative to the parent antibody.
Figure 4:
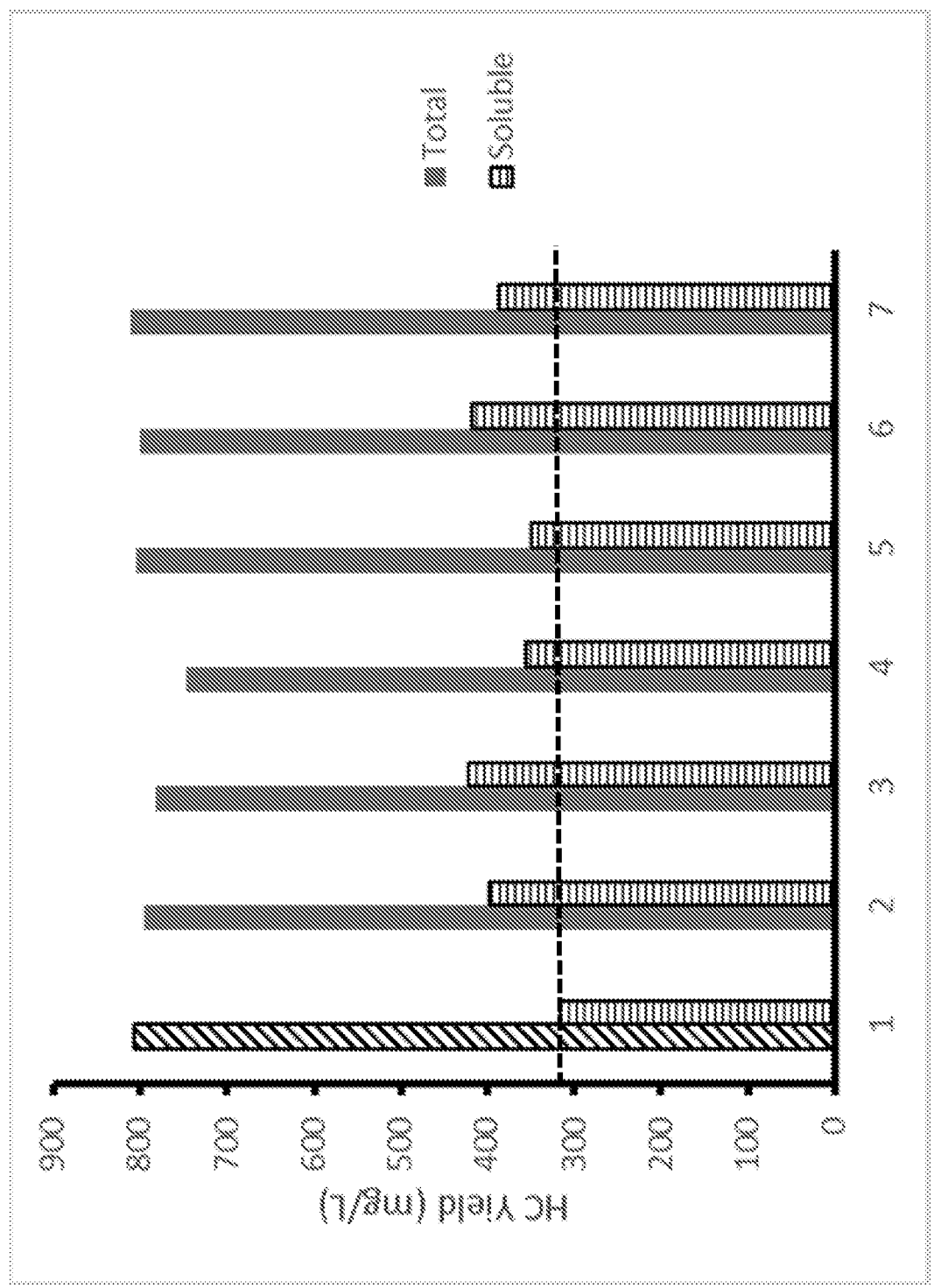
FIG. 4 is a bar chart illustrating solubility and total yield for an exemplary parent antibody and variants having single amino acid substitutions or combinations of amino acid substitutions relative to the parent antibody.

FIG. 3 illustrates the solubility of the heavy chain variants (x-axis labels "2" to "7") relative to the wild type antibody (x-axis label "1," diagonal stripes), and FIG. 4 illustrates both the total yield and the soluble yield of the heavy chain variants (x-axis labels "2" to "7") relative to the wild type antibody (x-axis label "1," where diagonal stripes indicate total yield for wild type). The soluble yield and the solubility of heavy chain variants were slightly improved.

Figure 5:
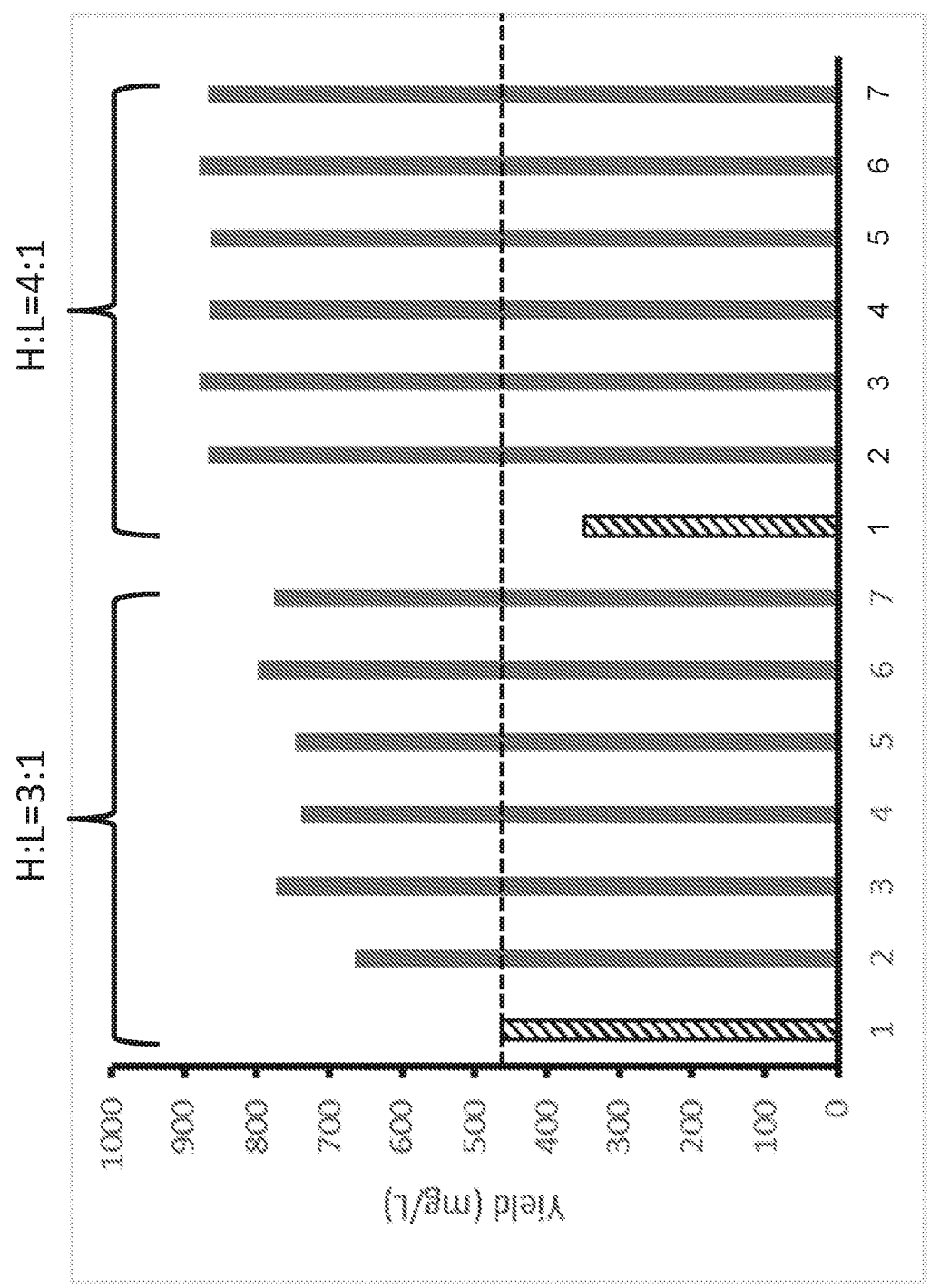
FIG. 5 is a bar chart showing overall yields for an exemplary parent antibody and variants having single amino acid substitutions or combinations of amino acid substitutions relative to the parent antibody. Data is provided for two separate heavy chain to light chain ratios.
Figure 6:
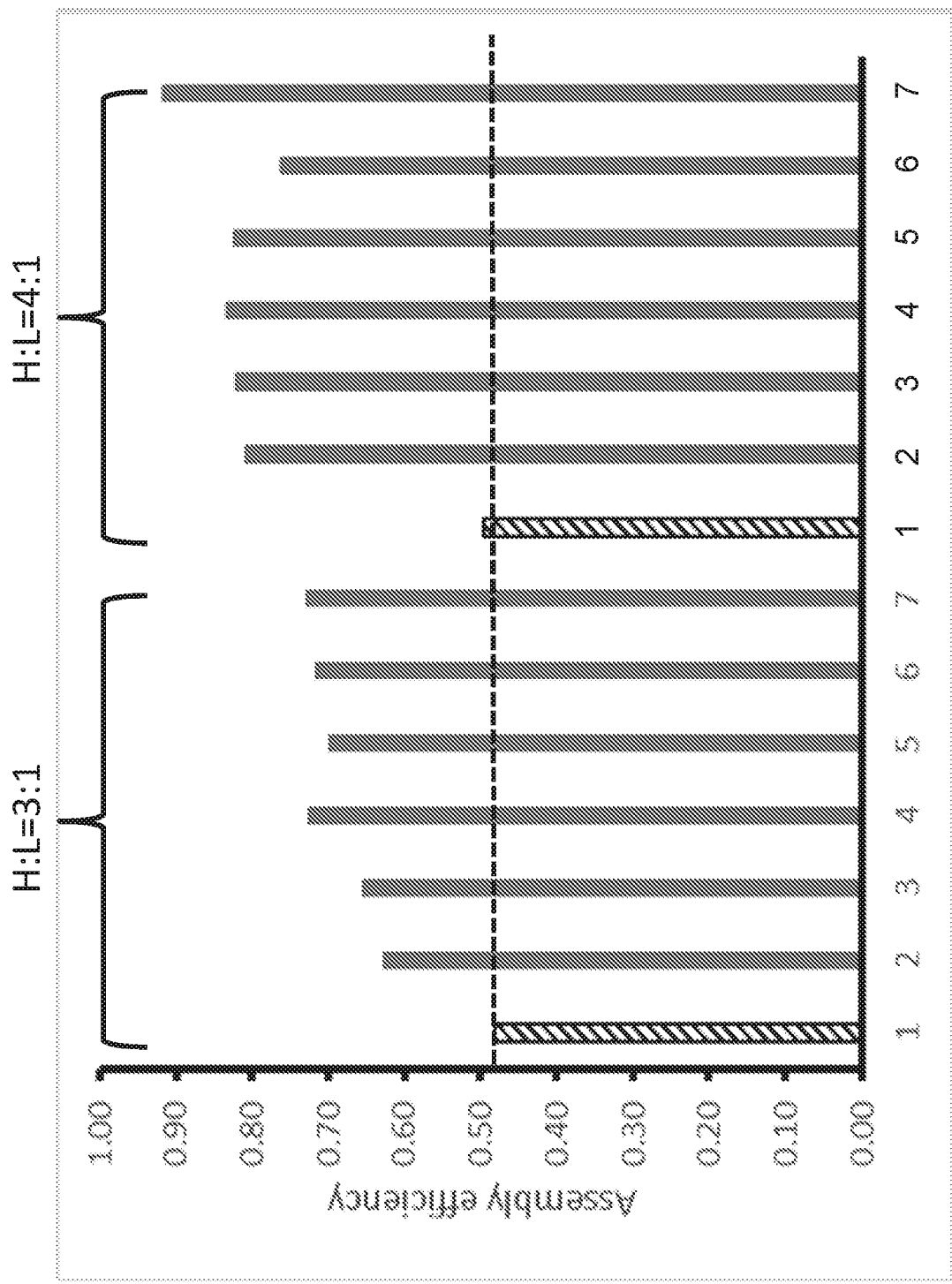
FIG. 6 is a bar chart showing assembly efficiency for an exemplary parent antibody and variants having single amino acid substitutions or combinations of amino acid substitutions relative to the parent antibody. Data is provided for two separate heavy chain to light chain ratios.

FIG. 5 and FIG. 6 illustrate that assembly efficiency was improved significantly with all six mutants tested. FIG. 5 illustrates the yield of antibody for each mutant (x-axis labels "2" to "7") using a heavy chain to light chain ratio (H:L) of 3:1 and 4:1, respectively. As shown in FIG. 5, the yields of the variants were similar at an H:L ratio of 4:1. FIG. 6 illustrates the assembly efficiency for each mutant (x-axis labels "2" to "7") using the same ratios ((H:L=3:1 or 4:1). As shown in FIG. 6, each CH2 variant demonstrated significantly improved assembly efficiency relative to the wild type antibody. At an H:L ratio of 4:1, the improvement in assembly efficiency in the CH2 variants ranged from about 50% to 80% improvement over the wild type antibody. Bars with diagonal stripes in FIG. 5 and FIG. 6 indicate measured values for the wild-type antibody.

Figure 7:
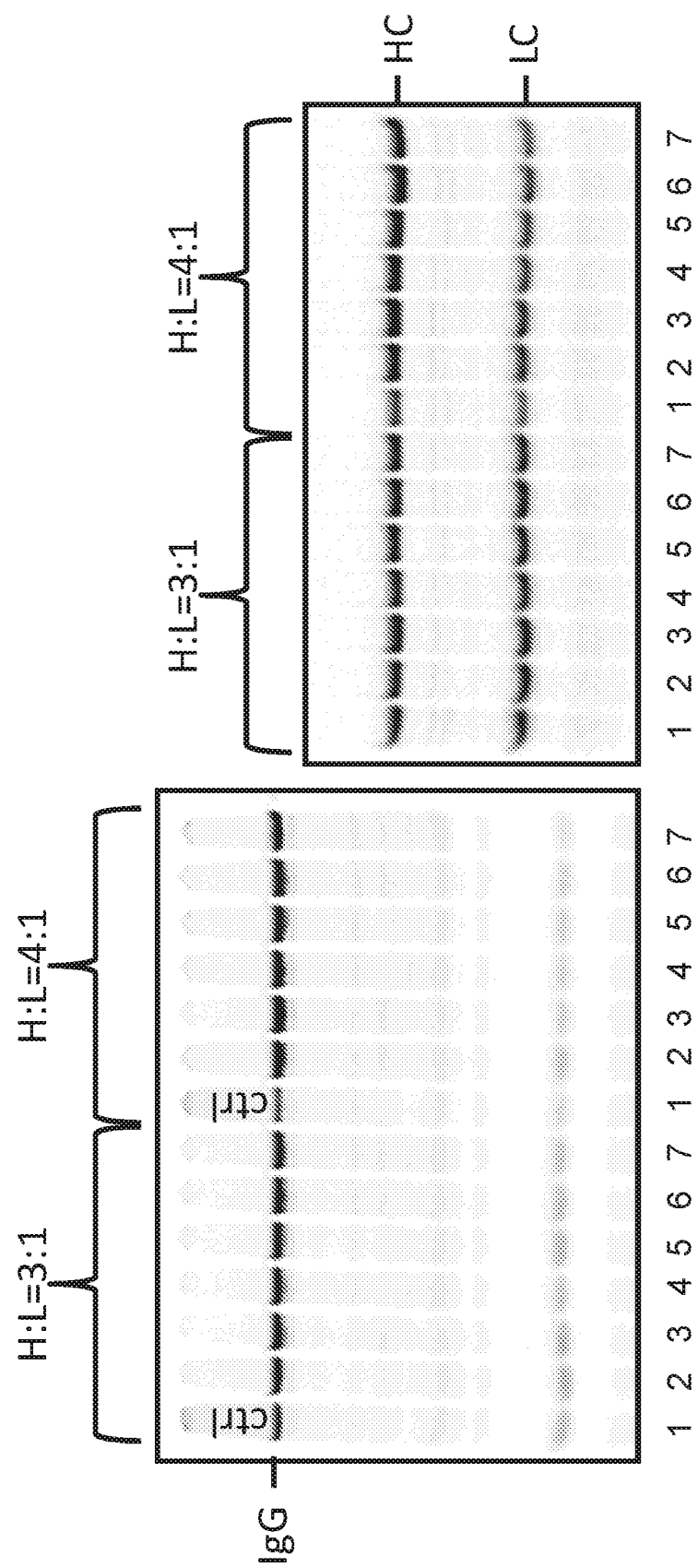
FIG. 7 is a $C^{14}$ autoradiogram for an exemplary parent antibody and variants having single amino acid substitutions or combinations of amino acid substitutions relative to the parent antibody. Data is provided for two separate heavy chain to light chain ratios.

FIG. 7 illustrates a $^{14}C$ non reducing (left) and reducing (right) autoradiogram of cell free expression of each mutant (individually labeled "2" to "7") using a heavy chain to light chain ratio (H:L) of 3:1 and 4:1, respectively.

Example 4

V262E Mutant Improves Assembly of an Aglycosylated Antibody

The V262E substitution was introduced into various examples of aglycosylated antibodies, and the yield and assembly efficiency of the resulting antibody was compared relative to the parent antibody.

Figure 8:
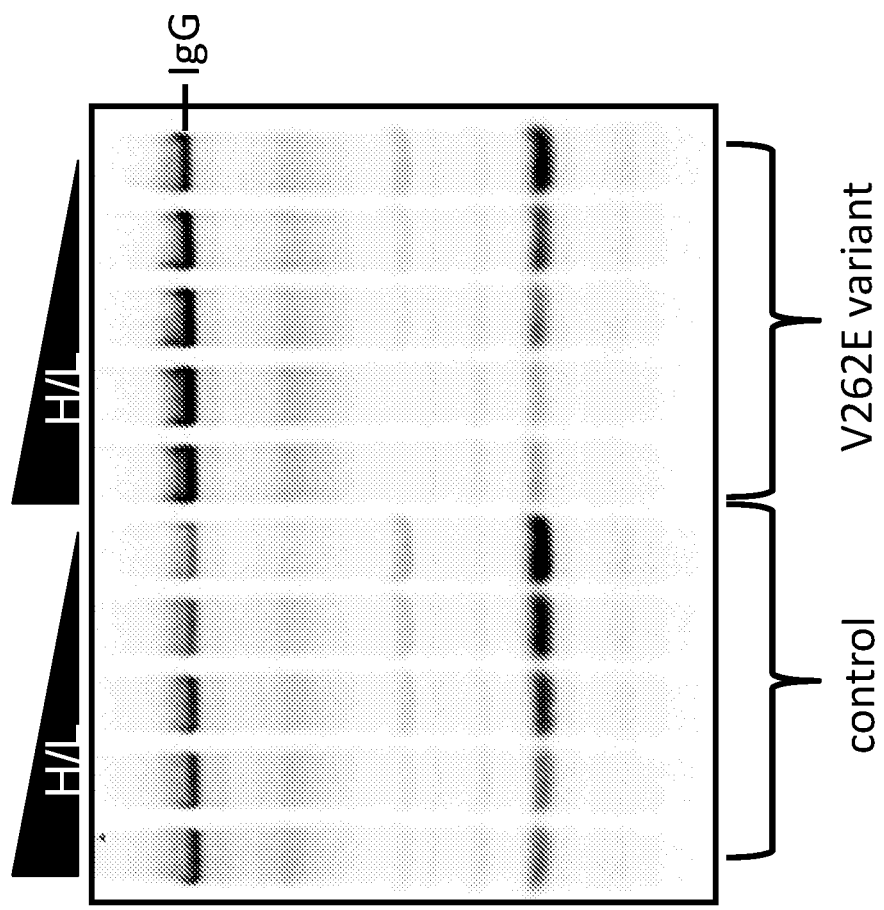
FIG. 8 is a $C^{14}$ autoradiogram for an exemplary parent antibody and a particular variant (V262E) over a range of heavy chain to light chain ratios (5:1 to 1:1).
Figure 9:
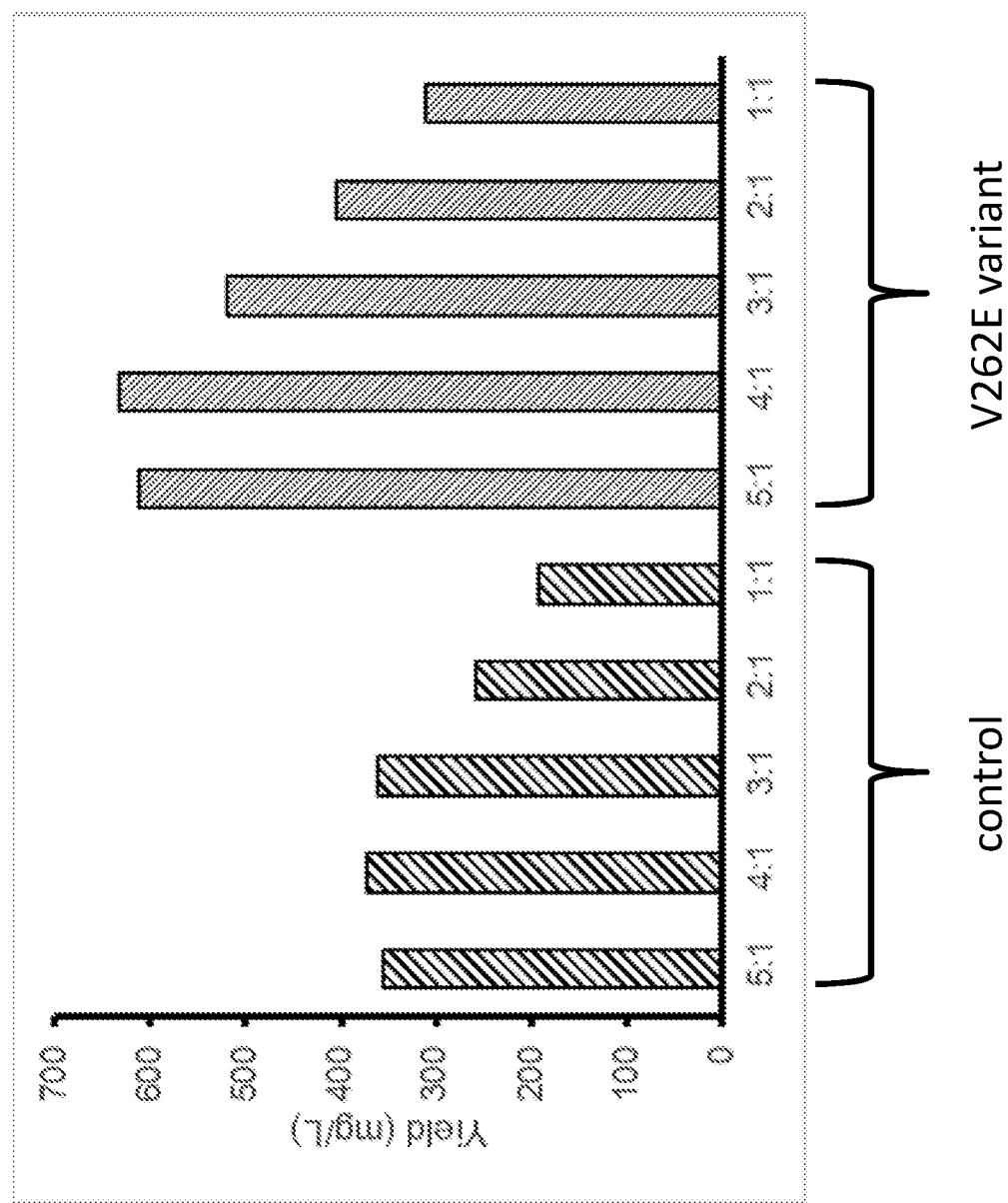
FIG. 9 is a bar chart showing overall yields for an exemplary parent antibody and a particular variant (V262E) over a range of heavy chain to light chain ratios (5:1 to 1:1).

In one example, the parent antibody was an aglycosylated anti-CD74 antibody with para-azido methyl phenylalanine (pAMF) incorporated into the heavy chain at position F404. FIG. 8 illustrates a C14 autoradiogram of the parent antibody and the V262E variant with heavy chain to light chain ratios (H:L) ranging from 5:1 to 1:1 from left to right. FIG. 9 illustrates the same information in quantitatively in a bar chart. As illustrated in FIG. 8 and FIG. 9, the V262E substitution variant demonstrates improved IgG assembled yield over the parent antibody by about 50%.

Figure 10:
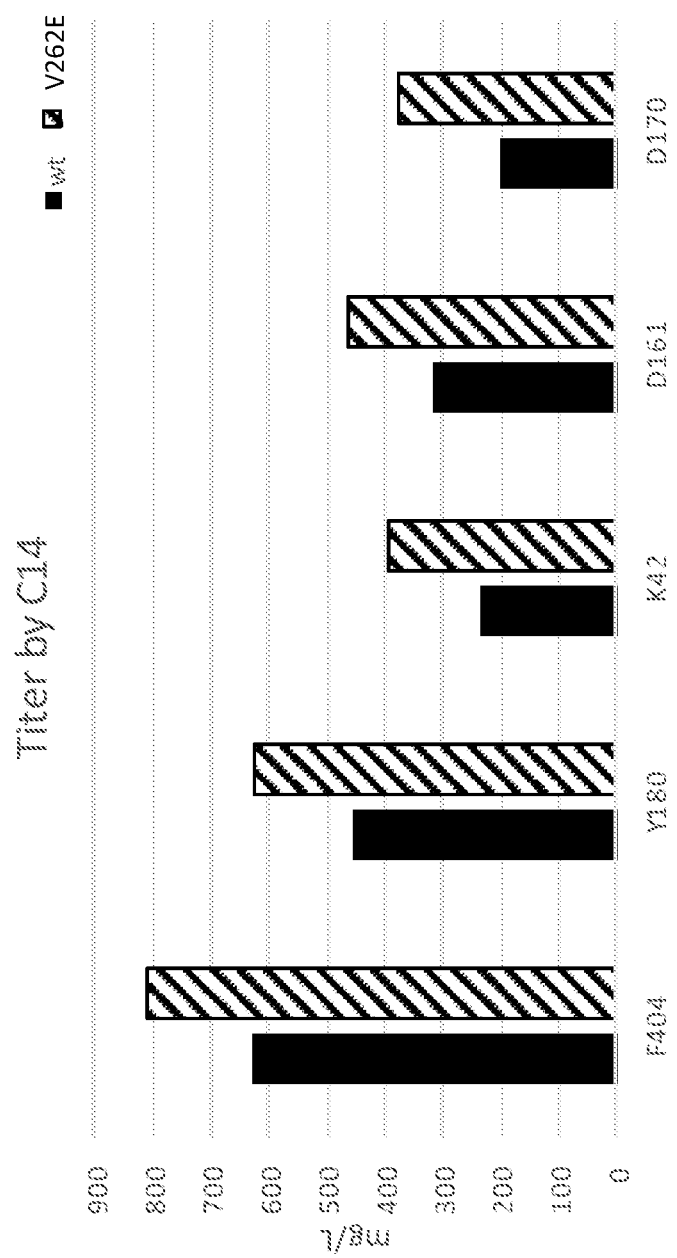
FIG. 10 is a bar chart illustrating IgG yield for each V262E antibody variant tested relative to its parent antibody, where each parent antibody also has a non-natural amino acid inserted at the individual positions shown in the x-axis of the figure.

In another example, an antibody was constructed as follows: The parent antibody was an aglycosylated antibody with para-azido methyl phenylalanine (pAMF) independently incorporated into the heavy chain at position Y180 or F404, or independently into the light chain at position K42, D161 or D170. FIG. 10 illustrates the comparison of optimal expression yields of the constructs without and with V262E mutation. As illustrated in FIG. 10, the V262E substitution variant demonstrates improved IgG assembled yield over the parent antibody with pAMF incorporated into each of the sites identified in the figure.

Figure 11:
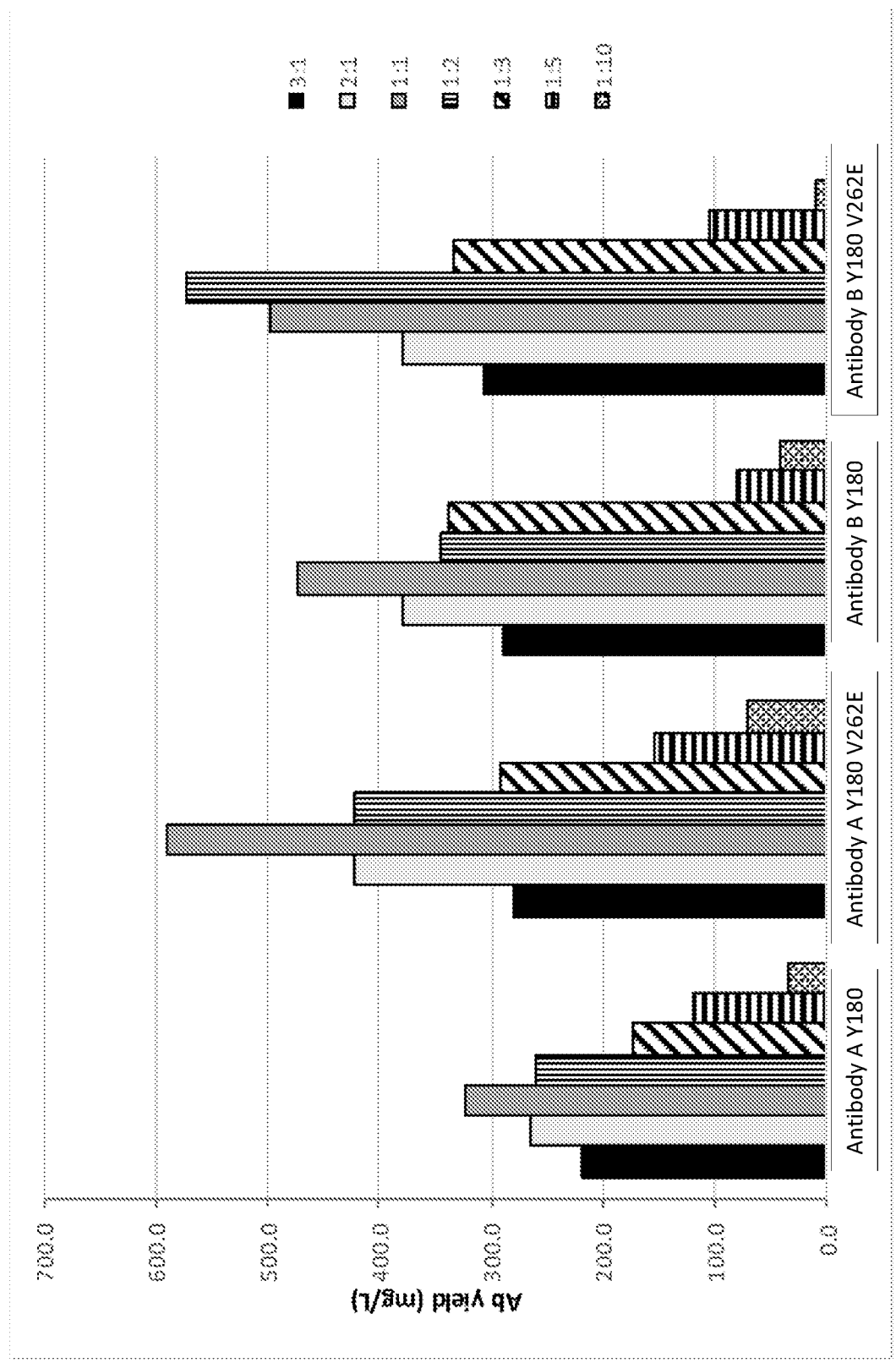
FIG. 11 is a bar chart illustrating IgG yield for each V262E antibody variant relative to its parent antibody (Antibodies A, B), where the parent antibody has a non-natural amino acid inserted at position Y180 in the heavy chain.

In another example, two antibodies were constructed as follows: The parent antibodies were two aglycosylated antibodies with para-azido methyl phenylalanine (pAMF) incorporated into the heavy chain at position Y180 ("Antibody A," "Antibody B"). FIG. 11 illustrates the expression yields of the parent antibody and the V262E variant with heavy chain to light chain ratios (H:L) ranging from 3:1 to 1:10 from left to right. As illustrated in FIG. 11, the V262E substitution variants demonstrate improved IgG assembled yield over the parent antibody by about 80% for Antibody A or 25% for Antibody B.

Figure 12:
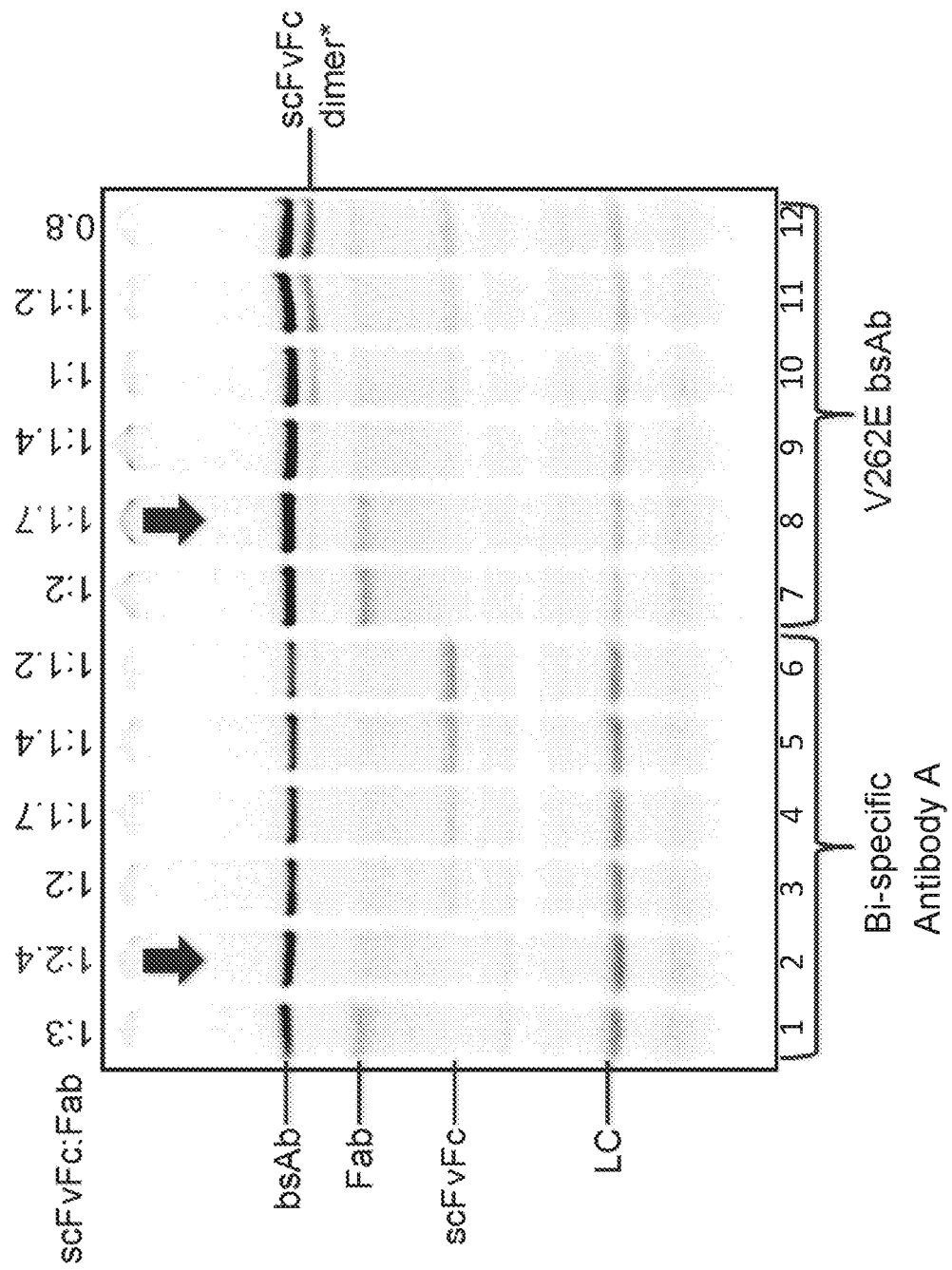
FIG. 12 is a C14 autoradiogram of IgG yields of bi-specific antibody (scFcFc×FabFc format, "Bi-specific Antibody A") and its V262E variant ("V262E bsAb") at various ratios of first antibody scFvFc:second antibody FabFc.
Figure 13:
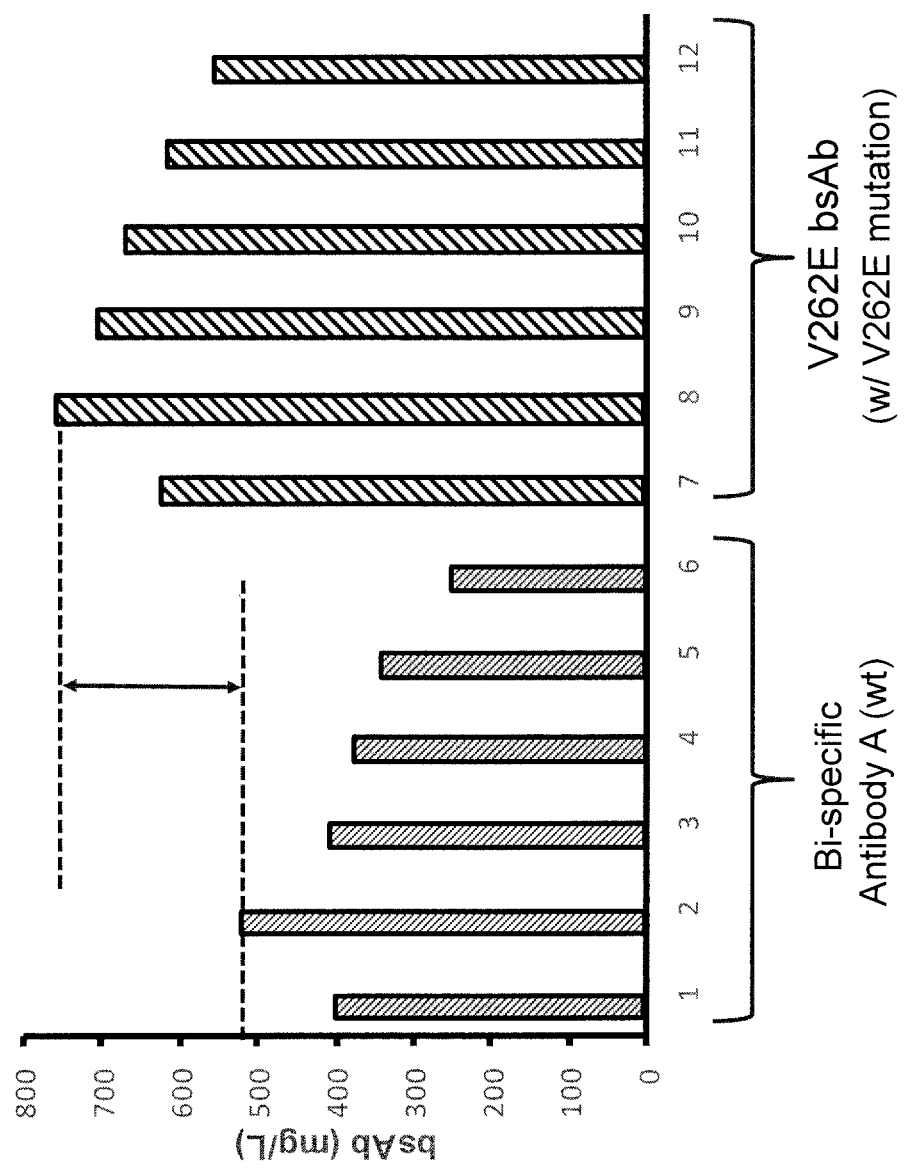
FIG. 13 is a bar chart that quantitatively illustrates the IgG yields of the bi-specific antibody ("Bi-specific Antibody A") and its V262E variant ("V262E bsAb") shown in FIG. 12.

In another example, a bi-specific antibody was constructed as follows: The parent antibody was an aglycosylated bi-specific antibody. The first antibody arm is in scFvFc format, while the second antibody arm is in FabFc format. FIG. 12 illustrates a C14 autoradiogram of the parent antibody and the V262E variant (V262E in both arms) with scFvFc to FabFc ratios shown in the figure. FIG. 13 illustrates the same information in quantitatively in a bar chart. As illustrated in FIGS. 12 and 13, the V262E substitution variant ("V262E bsAb") demonstrates improved IgG assembled yield over the parent antibody ("Bi-specific Antibody A") by about 60%.

Figure 14:
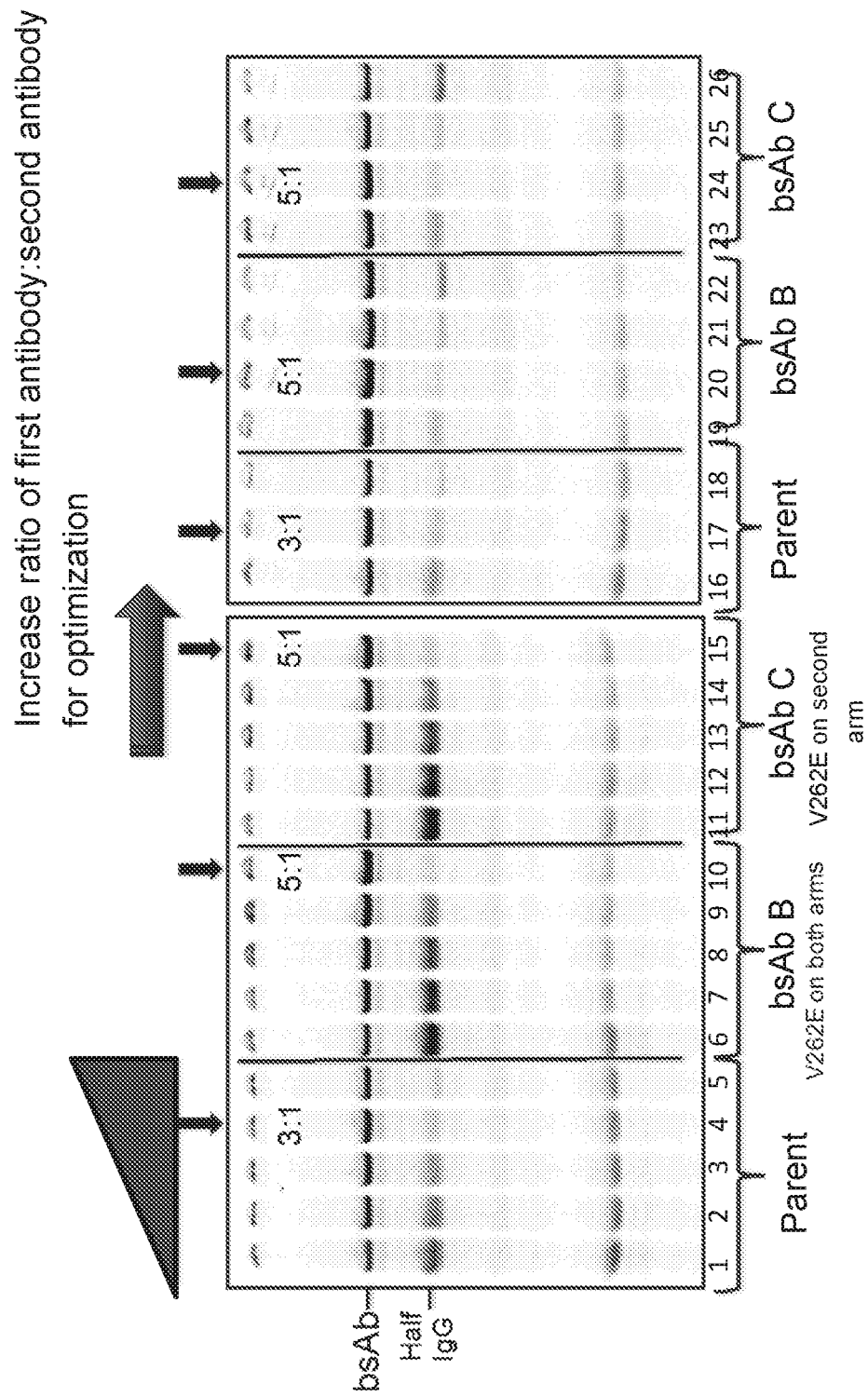
FIG. 14 is a C14 autoradiogram of IgG yields of a bi-specific antibody (FabFc×Fab Fc format, "Parent") and its V262E variants, where V262E was introduced into both arms ("bsAb B") or one arm ("bsAb C"), and where IgG yields were measured at various ratios of first antibody FabFc:second antibody FabFc.
Figure 15:
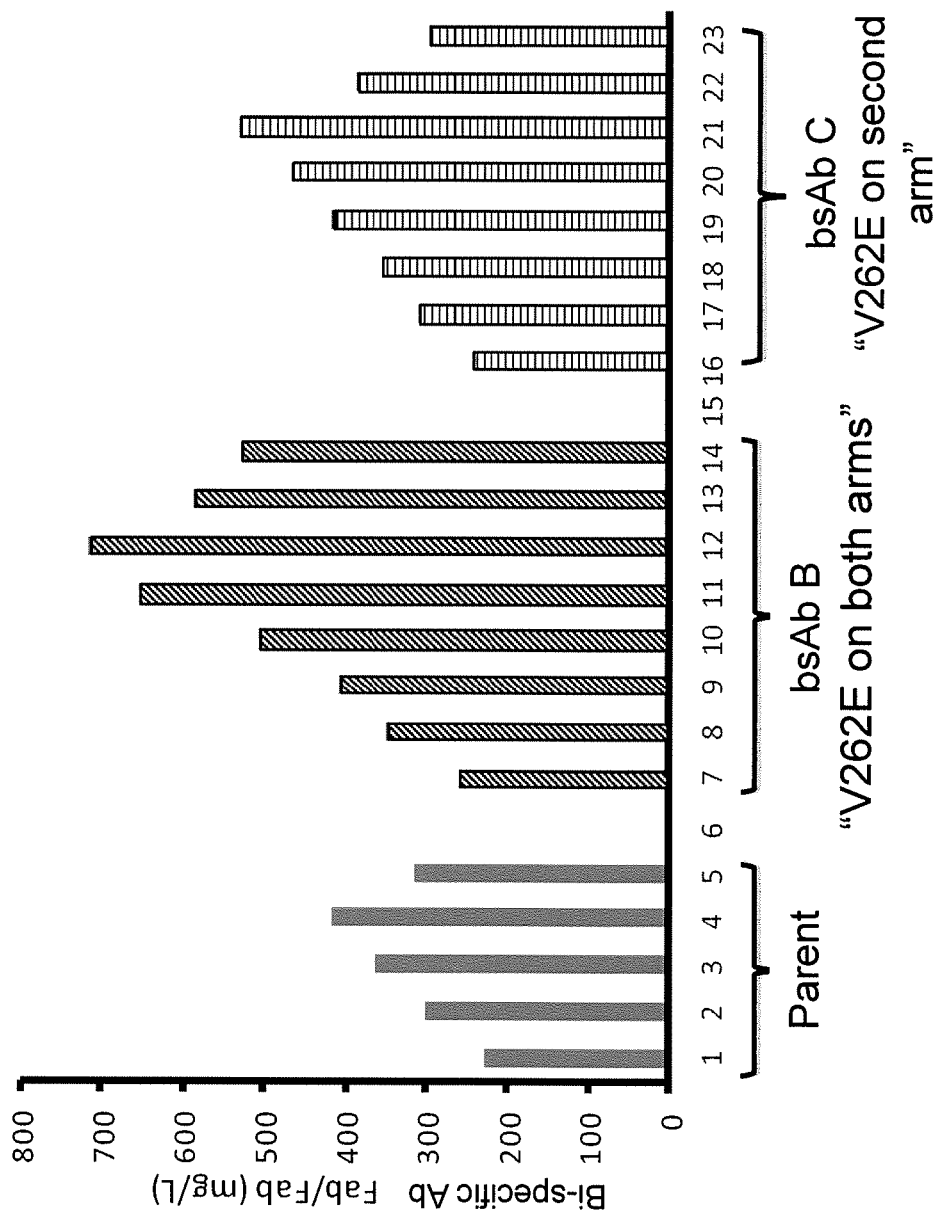
FIG. 15 is a bar chart quantitatively illustrates the IgG yields of the bi-specific antibody ("Parent") and its V262E variants ("bsAb B," "bsAb C") shown in FIG. 14.

In another example, bi-specific antibodies were constructed as follows: The parent antibody was an aglycosylated bi-specific antibody. Both the first antibody arm and the second antibody arm are in FabFc format. V262 was mutated to E on both arms ("bsAb B") or on the second antibody arm only ("bsAb C"). FIG. 14 illustrates a C14 autoradiogram of the parent antibody and the V262E variants with varying ratios of first antibody to second antibody arms shown in the figure. FIG. 15 illustrates the same information in quantitatively in a bar chart. As illustrated in FIGS. 14 and 15, the V262E variant with substitution on the second antibody arm (bsAb C) demonstrates improved IgG assembled yield over the parent antibody by about 25%. The V262E substitution on both arms variant (bsAb B) improves the yield further up to 60% over parent.

Example 5

Amino Acid Substitutions at Site V262

Various amino acids were substituted at position V262 in the CH2 domain of the heavy chain in trastuzumab. Mutations were cloned into trastuzumab as described in Example 1. Parent and variant antibodies were then scaled-up and purified separately in quadruplicate. Differential scanning fluorimetry (DSF) was performed with the final sample after purification. Table 8 includes the properties for the various amino acid substitutions tested in this example.

TABLE 8

Trastuzumab variants and their properties

| Antibody ID | Average Yield (µg/mL) | Standard Dev. | CV (%) | TM1, ° C. |
|---|---|---|---|---|
| WT | 820 | 72.0963 | 9% | 61.6 |
| WT | 797 | 44.0793 | 6% | 61.7 |
| V262D | 1559 | 104.403 | 7% | 51.4 |
| V262E | 2045 | 175.704 | 9% | 59.1 |
| V262K | 1298 | 120.059 | 9% | 54.6 |
| V262R | 604 | 373.064 | 62% | 52.2 |
| V262S | 1546 | 119.841 | 8% | 55.5 |

The results indicate that all variants exhibited improved yield over that of the parent antibody. However, of all the variants tested, the V262E was particularly robust in terms of maintaining thermal stability relative to that of the parent antibody. Accordingly, the V262E substitution appears to provide particular promise in terms of further investigation with respect to aglycosylated antibodies in general.

All publications, patents and patent applications cited in this specification are herein incorporated by reference as if each individual publication or patent application were specifically and individually indicated to be incorporated by reference.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of embodiments disclosed herein includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the present disclosure.

What is claimed:

1. An antibody of the IgG class with amino acid substitutions in the CH2 domain of the heavy chain comprising:
V262E, V264S, and V303R;
V262E, V264S, and V305R;
V262E, V303R, and V305R; or
V262E, V264S, V303R and V305R.

2. The antibody of claim 1, further comprising an amino acid substitution at position F241 and/or F243 of the CH2 domain.

3. The antibody of claim 1, wherein the antibody is aglycosylated.

4. The antibody of claim 1, further comprising one or more non-natural amino acid residues, wherein the one or more non-natural amino acid residues comprises a moiety selected from the group consisting of amino, carboxy, acetyl, hydrazine hydrazido, semicarbazido, sulfanyl, azido, alkynyl, and tetrazine.

5. The antibody of claim 1, wherein the antibody is a bi-specific antibody.

6. The antibody of claim 1, that is of the IgG1 subclass.

7. The antibody of claim 1, that is of the IgG2 subclass.

8. The antibody of claim 1 that is of the IgG4 subclass.

9. The antibody of claim 1 that is in a form selected from the group consisting of Fc, and full-length antibody.

10. The antibody of claim 4, wherein at least one non-natural amino acid is para-azido phenylalanine or para-azido methyl phenylalanine.

11. The antibody of claim 4 comprising two or more non-natural amino acid residues.

12. The antibody of claim 11, wherein a second non-natural amino acid residue is para-azido phenylalanine or para-azido methyl phenylalanine.

13. The antibody of claim 11, wherein at least one non-natural amino acid residue comprises a tetrazine moiety and at least second non-natural amino acid residue comprises an azide moiety.

14. An antibody conjugate comprising the antibody of claim 4 linked to one or more therapeutic moieties or labeling moieties by one or more non-natural amino acid residues.

15. The antibody conjugate of claim 14, wherein at least one of said therapeutic moieties or labeling moieties is linked to said antibody via a residue of a non-natural amino acid comprising an azide moiety.

16. The antibody conjugate of claim 14, wherein at least one of said therapeutic moieties or labeling moieties is linked to said antibody via a residue of the non-natural amino acid comprising a tetrazine moiety.

17. The antibody conjugate of claim 14, wherein at least one of said therapeutic moieties or labeling moieties is linked to said antibody via a residue of the non-natural amino acid comprising an azide moiety and at least one of said therapeutic moieties or labeling moieties is linked to said antibody via a residue of the non-natural amino acid comprising a tetrazine moiety.

18. The antibody conjugate of claim 14, wherein said antibody is linked to said one or more therapeutic moieties or labeling moieties via one or more linkers.

19. A composition comprising the antibody of claim 1, wherein said antibody is substantially pure.

20. A composition comprising the antibody of claim 1 wherein said antibody is at least 95% by mass of the total antibody mass of said composition.

21. A kit comprising an antibody of claim 1, and instructions for use of the antibody.

22. A kit comprising an antibody conjugate of claim 14, and instructions for use of the antibody.

23. A polynucleotide encoding an antibody of claim 1.

24. A vector comprising the polynucleotide of claim 23.

25. A host cell comprising the vector of claim 24.

* * * * *